(12) United States Patent
Kanamura et al.

(10) Patent No.: US 8,386,030 B2
(45) Date of Patent: Feb. 26, 2013

(54) IONTOPHORESIS DEVICE

(75) Inventors: Kiyoshi Kanamura, Shibuya-ku (JP);
Nobuharu Kosiba, Shibuya-ku (JP);
Mizuo Nakayama, Shibuya-ku (JP);
Takehiko Matsumura, Shibuya-ku (JP);
Hidero Akiyama, Shibuya-ku (JP);
Akihiko Matsumura, Shibuya-ku (JP)

(73) Assignee: TTI Ellebeau, Inc., Tokyo (JP)

( * ) Notice: Subject to any disclaimer, the term of this patent is extended or adjusted under 35 U.S.C. 154(b) by 1605 days.

(21) Appl. No.: 11/501,672

(22) Filed: Aug. 8, 2006

(65) Prior Publication Data

US 2007/0060859 A1 Mar. 15, 2007

Related U.S. Application Data

(60) Provisional application No. 60/717,970, filed on Sep. 15, 2005.

(30) Foreign Application Priority Data

Aug. 8, 2005 (JP) .................. 2005-229984
Dec. 16, 2005 (JP) .................. 2005-363085

(51) Int. Cl.
*A61N 1/30* (2006.01)
*A61M 31/00* (2006.01)
*A61F 13/00* (2006.01)

(52) U.S. Cl. ............... 604/20; 604/501; 424/449

(58) Field of Classification Search .......... 424/449; 604/20, 501

See application file for complete search history.

(56) References Cited

U.S. PATENT DOCUMENTS

| | | |
|---|---|---|
| 3,335,079 A | 8/1967 | Nellen |
| 3,645,884 A | 2/1972 | Gilliland |
| 3,891,786 A | 6/1975 | Conklin |
| 3,991,755 A | 11/1976 | Vernon et al. |
| 4,111,202 A | 9/1978 | Theeuwes |
| 4,116,889 A | 9/1978 | Chlanda et al. |
| 4,140,121 A | 2/1979 | Kühl et al. |
| 4,250,878 A | 2/1981 | Jacobsen et al. |
| 4,474,570 A | 10/1984 | Ariura et al. |
| 4,519,938 A | 5/1985 | Papir |
| 4,585,652 A | 4/1986 | Miller et al. ............... 424/83 |
| 4,640,689 A | 2/1987 | Sibalis |
| 4,691,718 A | 9/1987 | Sakuma et al. |

(Continued)

FOREIGN PATENT DOCUMENTS

| | | |
|---|---|---|
| CA | 2280046 | 8/1998 |
| EP | 0 097 436 | 1/1984 |

(Continued)

OTHER PUBLICATIONS

U.S. Appl. No. 11/541,399, filed Sep. 29, 2006, Carter.

(Continued)

*Primary Examiner* — Nicholas Lucchesi
*Assistant Examiner* — Ian Holloway
(74) *Attorney, Agent, or Firm* — Seed IP Law Group PLLC

(57) ABSTRACT

An iontophoresis device including an active electrode assembly or a counter electrode assembly with a polarizable electrode containing any one of a conductive material having a capacitance per unit weight of 1 F/g or greater, a conductive material having a specific surface area of 10 m2/g or greater, and activated carbon is disclosed. The generation of gas or ions due to an electrode reaction occurring in an electrode assembly may be reduced or prevented. In addition, the alteration of an active agent due to a chemical reaction upon energization may be reduced or prevented.

51 Claims, 14 Drawing Sheets

U.S. PATENT DOCUMENTS

| | | | |
|---|---|---|---|
| 4,702,732 A | 10/1987 | Powers et al. | |
| 4,708,716 A | 11/1987 | Sibalis | |
| 4,722,726 A | 2/1988 | Sanderson et al. | |
| 4,725,263 A | 2/1988 | McNichols et al. | 604/20 |
| 4,727,881 A | 3/1988 | Craighead et al. | |
| 4,731,049 A | 3/1988 | Parsi | |
| 4,744,787 A | 5/1988 | Phipps et al. | |
| 4,747,819 A | 5/1988 | Phipps et al. | |
| 4,752,285 A | 6/1988 | Petelenz et al. | |
| 4,764,164 A | 8/1988 | Sasaki | |
| 4,786,277 A | 11/1988 | Powers et al. | |
| 4,915,685 A | 4/1990 | Petelenz et al. | |
| 4,927,408 A | 5/1990 | Haak et al. | |
| 4,931,046 A | 6/1990 | Newman | |
| 4,940,456 A | 7/1990 | Sibalis et al. | |
| 4,944,296 A | 7/1990 | Suyama | |
| 4,969,983 A | 11/1990 | Parsi | |
| 5,006,108 A | 4/1991 | LaPrade | |
| 5,057,072 A | 10/1991 | Phipps | |
| 5,080,646 A | 1/1992 | Theeuwes et al. | |
| 5,084,006 A | 1/1992 | Lew et al. | |
| 5,084,008 A | 1/1992 | Phipps | |
| 5,135,477 A | 8/1992 | Untereker et al. | |
| 5,135,480 A | 8/1992 | Bannon et al. | |
| 5,147,296 A | 9/1992 | Theeuwes et al. | |
| 5,162,043 A | 11/1992 | Lew et al. | |
| 5,167,616 A | 12/1992 | Haak et al. | |
| 5,167,785 A | 12/1992 | McCready | |
| 5,169,383 A | 12/1992 | Gyory et al. | |
| 5,203,768 A | 4/1993 | Haak et al. | |
| 5,206,756 A | 4/1993 | Cheshire | 359/270 |
| 5,224,927 A | 7/1993 | Tapper | 604/20 |
| 5,238,613 A | 8/1993 | Anderson | |
| 5,244,557 A | 9/1993 | Defendini et al. | 204/192.29 |
| 5,246,417 A | 9/1993 | Haak et al. | |
| 5,298,017 A * | 3/1994 | Theeuwes et al. | 604/20 |
| 5,310,404 A | 5/1994 | Gyory et al. | |
| 5,312,326 A | 5/1994 | Myers et al. | |
| 5,320,598 A | 6/1994 | Haak et al. | |
| 5,322,502 A | 6/1994 | Theeuwes et al. | |
| 5,326,341 A | 7/1994 | Lew et al. | |
| 5,374,241 A | 12/1994 | Lloyd et al. | |
| 5,380,271 A | 1/1995 | Gyory | |
| 5,380,272 A | 1/1995 | Gross | |
| 5,385,543 A | 1/1995 | Haak et al. | |
| 5,395,310 A | 3/1995 | Untereker et al. | |
| 5,401,408 A | 3/1995 | Umemura et al. | |
| 5,405,317 A | 4/1995 | Myers et al. | |
| 5,425,703 A | 6/1995 | Feiring | |
| 5,445,606 A | 8/1995 | Haak et al. | |
| 5,464,387 A | 11/1995 | Haak et al. | |
| 5,496,266 A | 3/1996 | Haak et al. | |
| 5,503,632 A | 4/1996 | Haak | |
| 5,511,548 A | 4/1996 | Riazzi et al. | |
| 5,543,098 A | 8/1996 | Myers et al. | |
| 5,551,953 A | 9/1996 | Lattin et al. | |
| 5,558,633 A * | 9/1996 | Phipps et al. | 604/20 |
| 5,573,503 A | 11/1996 | Untereker et al. | |
| 5,573,668 A | 11/1996 | Grosh et al. | |
| 5,582,587 A | 12/1996 | Gyory et al. | |
| 5,605,536 A | 2/1997 | Sibalis | |
| 5,618,265 A | 4/1997 | Myers et al. | |
| 5,620,580 A | 4/1997 | Okabe et al. | |
| 5,623,157 A | 4/1997 | Miyazaki et al. | |
| 5,637,084 A | 6/1997 | Kontturi et al. | |
| 5,646,815 A | 7/1997 | Owens et al. | |
| 5,647,844 A | 7/1997 | Haak et al. | |
| 5,668,170 A | 9/1997 | Gyory | |
| 5,685,837 A | 11/1997 | Horstmann | |
| 5,709,882 A | 1/1998 | Lindstedt et al. | |
| 5,711,761 A | 1/1998 | Untereker et al. | |
| 5,723,130 A | 3/1998 | Hancock et al. | |
| 5,725,817 A | 3/1998 | Milder | |
| 5,730,716 A | 3/1998 | Beck et al. | |
| 5,738,647 A | 4/1998 | Bernhard et al. | |
| 5,746,711 A | 5/1998 | Sibalis et al. | |
| 5,788,666 A | 8/1998 | Atanasoska | |
| 5,817,044 A | 10/1998 | Evers et al. | 604/20 |
| 5,837,226 A | 11/1998 | Jungherr et al. | |
| 5,840,056 A | 11/1998 | Atanasoska | |
| 5,840,339 A | 11/1998 | Kunin | |
| 5,871,460 A | 2/1999 | Phipps et al. | |
| 5,919,155 A | 7/1999 | Lattin et al. | 604/20 |
| 5,928,185 A * | 7/1999 | Muller et al. | 604/20 |
| 5,941,843 A | 8/1999 | Atanasoska et al. | |
| 5,976,101 A | 11/1999 | Sibalis | |
| 5,991,655 A | 11/1999 | Gross et al. | 604/20 |
| 5,993,435 A | 11/1999 | Haak et al. | |
| 5,995,869 A | 11/1999 | Cormier et al. | |
| 6,006,130 A | 12/1999 | Higo et al. | |
| 6,009,345 A | 12/1999 | Hofmann | |
| 6,032,073 A | 2/2000 | Effenhauser | |
| 6,047,208 A | 4/2000 | Flower | |
| 6,049,733 A | 4/2000 | Phipps et al. | |
| 6,064,908 A * | 5/2000 | Muller et al. | 604/20 |
| 6,086,572 A | 7/2000 | Johnson et al. | |
| 6,103,078 A | 8/2000 | Hitchems et al. | |
| 6,109,852 A | 8/2000 | Shahinpoor et al. | |
| 6,163,720 A | 12/2000 | Gyory et al. | |
| 6,167,302 A | 12/2000 | Millot | |
| 6,169,920 B1 | 1/2001 | Haak et al. | |
| 6,195,582 B1 | 2/2001 | Scott | |
| 6,223,075 B1 | 4/2001 | Beck et al. | 604/20 |
| 6,228,206 B1 | 5/2001 | Herman et al. | |
| 6,258,276 B1 | 7/2001 | Mika et al. | |
| 6,289,241 B1 * | 9/2001 | Phipps | 604/20 |
| 6,314,317 B1 | 11/2001 | Willis | |
| 6,317,630 B1 | 11/2001 | Gross et al. | |
| 6,327,496 B1 | 12/2001 | Hamlin et al. | |
| 6,329,488 B1 | 12/2001 | Terry et al. | |
| 6,330,471 B1 | 12/2001 | Higo et al. | |
| 6,335,266 B1 | 1/2002 | Kitahara et al. | 438/475 |
| 6,336,049 B1 | 1/2002 | Kinbara et al. | |
| 6,350,259 B1 | 2/2002 | Sage, Jr. et al. | |
| 6,374,136 B1 | 4/2002 | Murdock | |
| 6,377,847 B1 | 4/2002 | Keusch et al. | |
| 6,377,848 B1 | 4/2002 | Garde et al. | |
| 6,385,488 B1 | 5/2002 | Flower et al. | |
| 6,394,994 B1 | 5/2002 | Vilambi et al. | |
| 6,402,732 B1 | 6/2002 | Flower et al. | |
| 6,405,875 B1 | 6/2002 | Cutler | |
| 6,421,561 B1 | 7/2002 | Morris | |
| 6,454,941 B1 | 9/2002 | Cutler et al. | |
| 6,462,935 B1 | 10/2002 | Shiue et al. | |
| 6,468,657 B1 | 10/2002 | Hou et al. | 428/403 |
| 6,477,410 B1 | 11/2002 | Henley et al. | |
| 6,496,727 B1 | 12/2002 | Bernhard et al. | |
| 6,497,887 B1 | 12/2002 | Zecchino et al. | |
| 6,503,957 B1 | 1/2003 | Bernatowicz et al. | |
| 6,505,069 B2 | 1/2003 | Scott et al. | |
| 6,522,919 B1 | 2/2003 | Flower et al. | |
| 6,532,386 B2 | 3/2003 | Sun et al. | 604/20 |
| 6,553,253 B1 | 4/2003 | Chang | |
| 6,553,255 B1 | 4/2003 | Miller et al. | |
| 6,560,483 B1 | 5/2003 | Kumar et al. | |
| 6,564,092 B1 | 5/2003 | Nakamura et al. | |
| 6,584,349 B1 | 6/2003 | Sage, Jr. et al. | |
| 6,597,947 B1 | 7/2003 | Inoue et al. | |
| 6,629,968 B1 | 10/2003 | Jain et al. | |
| 6,635,045 B2 | 10/2003 | Keusch et al. | |
| 6,654,635 B1 | 11/2003 | Koga et al. | |
| 6,678,554 B1 | 1/2004 | Sun et al. | |
| 6,678,555 B2 | 1/2004 | Flower et al. | |
| 6,692,456 B1 | 2/2004 | Eppstein et al. | |
| 6,708,050 B2 | 3/2004 | Carim | |
| 6,725,090 B1 | 4/2004 | Lattin et al. | 604/20 |
| 6,731,977 B2 | 5/2004 | Beck | |
| 6,731,987 B1 | 5/2004 | McAdams et al. | |
| 6,735,470 B2 | 5/2004 | Henley et al. | |
| 6,743,015 B2 | 6/2004 | Magnani | |
| 6,743,432 B1 | 6/2004 | Yanai et al. | 424/400 |
| 6,745,071 B1 | 6/2004 | Anderson et al. | |
| 6,775,569 B2 | 8/2004 | Mori et al. | 604/20 |
| 6,775,570 B2 | 8/2004 | Joshi | |
| 6,858,018 B1 * | 2/2005 | Green et al. | 604/19 |
| 6,862,473 B2 | 3/2005 | Keusch et al. | |
| 6,915,159 B1 | 7/2005 | Kuribayashi et al. | |

| | | |
|---|---|---|
| 6,918,901 B1 | 7/2005 | Theeuwes et al. |
| 6,975,902 B2 | 12/2005 | Phipps et al. |
| 7,018,370 B2 | 3/2006 | Southam et al. |
| 7,033,598 B2 | 4/2006 | Lerner |
| 7,047,069 B2 | 5/2006 | Joshi |
| 7,054,682 B2 | 5/2006 | Young et al. ............... 604/20 |
| 7,127,285 B2 | 10/2006 | Henley et al. ............... 604/20 |
| 7,392,080 B2 | 6/2008 | Eppstein et al. ............ 604/20 |
| 7,398,121 B2 | 7/2008 | Matsumura et al. ......... 604/20 |
| 2002/0016562 A1 | 2/2002 | Cormier et al. |
| 2002/0022795 A1 | 2/2002 | Reynolds et al. |
| 2002/0055704 A1 | 5/2002 | Scott et al. |
| 2002/0099320 A1 | 7/2002 | Beck |
| 2002/0110739 A1 | 8/2002 | McEwen et al. |
| 2002/0123678 A1 | 9/2002 | Lerner et al. |
| 2002/0188241 A1 | 12/2002 | Morris et al. ............... 604/20 |
| 2003/0018295 A1 | 1/2003 | Henley et al. |
| 2003/0052015 A1 | 3/2003 | Becker et al. ............... 205/414 |
| 2003/0088204 A1 | 5/2003 | Joshi |
| 2003/0088205 A1 | 5/2003 | Chandrasekaran et al. ... 604/20 |
| 2003/0135150 A1 | 7/2003 | Kuribayashi et al. |
| 2003/0168404 A1 | 9/2003 | Mika et al. |
| 2003/0191426 A1 | 10/2003 | Lerner et al. |
| 2003/0199808 A1 | 10/2003 | Henley et al. |
| 2003/0208152 A1 | 11/2003 | Avrahami ................... 604/20 |
| 2003/0212397 A1 | 11/2003 | Avrahami |
| 2004/0071765 A1 | 4/2004 | Adachi et al. |
| 2004/0105881 A1 | 6/2004 | Cevc et al. |
| 2004/0138609 A1 | 7/2004 | Fukuta et al. |
| 2004/0143210 A1 | 7/2004 | Shevlin |
| 2004/0167459 A1 | 8/2004 | Higuchi et al. |
| 2004/0176737 A1 | 9/2004 | Henley et al. |
| 2004/0176803 A1 | 9/2004 | Whelan et al. |
| 2004/0176805 A1 | 9/2004 | Whelan et al. |
| 2004/0225253 A1 | 11/2004 | Shevlin ...................... 604/20 |
| 2004/0267169 A1 | 12/2004 | Sun et al. |
| 2004/0267232 A1 | 12/2004 | Sun et al. |
| 2004/0267236 A1 | 12/2004 | Sun et al. |
| 2005/0004506 A1 | 1/2005 | Gyory |
| 2005/0011826 A1 | 1/2005 | Childs et al. |
| 2005/0070840 A1 | 3/2005 | Matsumura et al. |
| 2005/0131336 A1 | 6/2005 | Mori et al. |
| 2005/0143686 A1 | 6/2005 | Shevlin ...................... 604/20 |
| 2005/0148996 A1 | 7/2005 | Sun et al. |
| 2005/0169976 A1* | 8/2005 | Mori et al. ................... 424/449 |
| 2005/0193554 A1 | 9/2005 | Young et al. |
| 2005/0215944 A1 | 9/2005 | Young et al. |
| 2005/0267440 A1 | 12/2005 | Herman et al. |
| 2005/0287201 A1 | 12/2005 | Till et al. .................... 424/450 |
| 2006/0009730 A2 | 1/2006 | Shevlin ...................... 604/20 |
| 2006/0036209 A1 | 2/2006 | Subramony et al. |
| 2006/0052739 A1 | 3/2006 | Henley et al. |
| 2006/0083962 A1 | 4/2006 | Takekawa et al. ............ 429/13 |
| 2006/0089591 A1 | 4/2006 | Nagashima et al. |
| 2006/0095001 A1 | 5/2006 | Matsumura et al. |
| 2006/0116628 A1 | 6/2006 | Matsumura et al. |
| 2006/0129085 A1 | 6/2006 | Tanioka et al. |
| 2006/0135906 A1 | 6/2006 | Matsumura et al. |
| 2006/0173401 A1 | 8/2006 | Tanioka et al. |
| 2006/0198879 A1 | 9/2006 | Fukuta et al. |
| 2006/0211980 A1 | 9/2006 | Cormier et al. |
| 2006/0217654 A1 | 9/2006 | Matsumura et al. |
| 2006/0241548 A1 | 10/2006 | Fukuta et al. |
| 2006/0247364 A1 | 11/2006 | Murray et al. ............... 524/495 |
| 2006/0260955 A1* | 11/2006 | Sasaki et al. ................ 205/759 |
| 2006/0276742 A1 | 12/2006 | Matsumura et al. |
| 2007/0021711 A1 | 1/2007 | Matsumura et al. |
| 2007/0027426 A1 | 2/2007 | Matsumura et al. |
| 2007/0031730 A1* | 2/2007 | Kawakami et al. .......... 429/218.1 |
| 2007/0048362 A1 | 3/2007 | Nakayama et al. |
| 2007/0060859 A1 | 3/2007 | Kanamura et al. |
| 2007/0060860 A1 | 3/2007 | Nakayama et al. |
| 2007/0060862 A1* | 3/2007 | Sun et al. .................... 604/20 |
| 2007/0066930 A1 | 3/2007 | Tanioka et al. |
| 2007/0066931 A1 | 3/2007 | Kanamura et al. |
| 2007/0066932 A1 | 3/2007 | Akiyama et al. |
| 2007/0071807 A1 | 3/2007 | Akiyama et al. |
| 2007/0073212 A1 | 3/2007 | Matsumura |
| 2007/0074590 A1 | 4/2007 | Smith |
| 2007/0078374 A1 | 4/2007 | Smith |
| 2007/0078375 A1 | 4/2007 | Smith |
| 2007/0078376 A1 | 4/2007 | Smith |
| 2007/0083186 A1 | 4/2007 | Carter et al. |
| 2007/0088332 A1 | 4/2007 | Akiyama et al. |
| 2007/0093787 A1 | 4/2007 | Smith |
| 2007/0100274 A1* | 5/2007 | Young et al. ................ 604/20 |
| 2007/0112294 A1 | 5/2007 | Akiyama et al. |
| 2007/0135754 A1 | 6/2007 | Akiyama et al. |
| 2007/0139862 A1* | 6/2007 | Tateishi et al. .............. 361/502 |
| 2007/0197955 A1 | 8/2007 | Akiyama et al. |
| 2007/0213652 A1 | 9/2007 | Carter |
| 2007/0232983 A1 | 10/2007 | Smith |
| 2007/0255195 A1 | 11/2007 | Adachi |
| 2007/0270733 A1 | 11/2007 | Nagashima et al. |
| 2008/0033338 A1 | 2/2008 | Smith |
| 2008/0033398 A1 | 2/2008 | Reed et al. |
| 2008/0154178 A1 | 6/2008 | Carter et al. |
| 2008/0213646 A1 | 9/2008 | Takekawa et al. ............ 429/33 |

FOREIGN PATENT DOCUMENTS

| | | |
|---|---|---|
| EP | 0 411 146 A1 | 2/1991 |
| EP | 0 504 715 | 9/1992 |
| EP | 0 824 003 | 2/1998 |
| EP | 0 931 564 A1 | 7/1999 |
| EP | 1 440 707 A1 | 7/2004 |
| EP | 1 566 197 A1 | 8/2005 |
| GB | 2 265 088 A | 9/1993 |
| JP | 52-151720 | 12/1977 |
| JP | 60-35936 | 2/1985 |
| JP | 63-35266 | 2/1988 |
| JP | 3-94771 | 4/1991 |
| JP | 3-504343 | 9/1991 |
| JP | 5-20385 | 8/1993 |
| JP | 7-504110 | 5/1995 |
| JP | 08-052224 | 2/1996 |
| JP | 08-503875 | 4/1996 |
| JP | 09-201420 | 8/1997 |
| JP | 9-248344 | 9/1997 |
| JP | 2-801083 | 7/1998 |
| JP | 2792661 | 9/1998 |
| JP | 2845509 | 10/1998 |
| JP | 11-19226 | 1/1999 |
| JP | 11-123246 | 5/1999 |
| JP | 2901348 | 6/1999 |
| JP | 11-239621 | 9/1999 |
| JP | 3-40517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2000-316991 | 11/2000 |
| JP | 2001-070459 | 3/2001 |
| JP | 2001-505091 | 4/2001 |
| JP | 2001-120670 | 5/2001 |
| JP | 2002-233584 | 8/2002 |
| JP | 2002-536133 | 10/2002 |
| JP | 3406315 | 3/2003 |
| JP | 2003-299743 | 10/2003 |
| JP | 2004-188188 | 7/2004 |
| JP | 2004-202057 | 7/2004 |
| JP | 2004-292438 | 10/2004 |
| JP | 2004-317317 | 10/2004 |
| JP | 2004-357313 | 12/2004 |
| JP | 2006-149891 | 6/2006 |
| JP | 2006-212194 | 8/2006 |
| JP | 2007-037639 | 2/2007 |
| JP | 2007-037640 | 2/2007 |
| JP | 2007-050136 | 3/2007 |
| JP | 2007-075327 | 3/2007 |
| WO | WO 90/03825 | 4/1990 |
| WO | WO 90/04433 | 5/1990 |
| WO | 90/08571 | 8/1990 |
| WO | WO 90/08571 | 8/1990 |
| WO | WO 91/16943 | 11/1991 |

| | | |
|---|---|---|
| WO | 93/18727 | 9/1993 |
| WO | 94/22528 | 10/1994 |
| WO | WO 95/35132 | 12/1995 |
| WO | 96/10440 | 4/1996 |
| WO | 97/11744 | 4/1997 |
| WO | WO 97/47353 | 12/1997 |
| WO | WO 97/48444 | 12/1997 |
| WO | WO 98/35722 | 8/1998 |
| WO | 99/38565 | 8/1999 |
| WO | WO 00/47274 | 8/2000 |
| WO | WO 00/66216 | 11/2000 |
| WO | WO 01/39830 | 6/2001 |
| WO | WO 03/008078 | 1/2003 |
| WO | WO 03/037425 | 5/2003 |
| WO | WO 03/061758 | 7/2003 |
| WO | WO 2004/028626 | 4/2004 |
| WO | WO 2004/073843 | 9/2004 |
| WO | WO 2005/120631 | 12/2005 |
| WO | WO 2006/046703 | 5/2006 |
| WO | WO 2006/062108 | 6/2006 |
| WO | WO 2008/027218 | 3/2008 |

OTHER PUBLICATIONS

U.S. Appl. No. 60/718,175, filed Sep. 15, 2005, Matsumura et al.
U.S. Appl. No. 60/719,478, filed Sep. 15, 2005, Mitsuguchi et al.
U.S. Appl. No. 60/720,719, filed Sep. 26, 2005, Nakayama et al.
U.S. Appl. No. 60/720,781, filed Sep. 26, 2005, Nakayama et al.
U.S. Appl. No. 60/728,462, filed Oct. 20, 2005, Akiyama et al.
U.S. Appl. No. 60/728,563, filed Oct. 20, 2005, Nakayama et al.
U.S. Appl. No. 60/729,451, filed Oct. 21, 2005, Nakayama et al.
U.S. Appl. No. 60/729,563, filed Oct. 24, 2005, Matsumura et al.
U.S. Appl. No. 60/730,156, filed Oct. 24, 2005, Tanioka et al.
U.S. Appl. No. 60/730,159, filed Oct. 24, 2005, Akiyama et al.
Cabovska, B., "Investigations of Separation Mechanisms in Capillary Electrophoresis and High Performance Liquid Chromatography." (2004) Proquest. UMI No. 3120882.
Ito, Y., et al. "In vitro Effect of Ion Exchange Membrane on Iontophoresis," *Medicine and Biology*, 147(3):41-46, 2003.
JIS (Japanese Industrial Standards), "Testing Methods for Bubble Point of Membrane Filters," K3832-1990.
Ogata, N., "Dodensei Kobunshi" (Electrically Conductive High Molecular Compounds), Kodansha Scientific, (1990).
Kalia, Y., et al., "Iontophoretic Drug Delivery," *Advanced Drug Delivery Reviews*, 56:619-658, 2004.

* cited by examiner

IONTOPHORESIS DEVICE

BACKGROUND

1. Field

The present disclosure generally relates to the field of iontophoresis, and in particular, to an iontophoresis device capable of preventing or suppressing an electrode reaction in an electrode assembly.

2. Description of the Related Art

JP 3030517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A, and WO 03/037425, the disclosures of which are incorporated herein by reference, disclose iontophoresis devices for administering an active agent capable of dissociating into ions (active agent ions) of positive or negative polarity.

Iontophoresis involves driving an active agent dissociated to positive or negative ions in solution by using an electrical potential to transdermally transfer the active agent into a subject, and may be advantageous such as reducing the burden placed on a subject, or improving controllability of the amount of the active agent to be administered.

FIG. 9 is an explanatory view showing the basic configuration of an iontophoresis device for performing iontophoresis.

The iontophoresis device comprises: an active electrode assembly 110 having an electrode 111 and an active agent solution reservoir 114 that holds a solution of an active agent which dissociates into positive or negative active agent ions (an active agent solution); a counter electrode assembly 120 having an electrode 121 and an electrolyte solution reservoir 122 that holds an electrolyte solution; and an electric power source 130 that includes terminals connected to the electrodes 111 and 121. An electrical potential having the same polarity as that of an active agent ion is applied to the electrode 111 and an electrical potential having a polarity opposite to that of the active agent ions is applied to the electrode 121 when the active agent solution reservoir 114 and the electrolyte solution reservoir 122 are brought into contact with the biological interface of a subject, thus delivering the active agent ions to the subject.

One issue to be investigated in such iontophoresis devices concerns various electrode reactions that may occur in the electrode assemblies 110 and 120.

For example, when an active agent is a cationic active agent that dissociates into positive active agent ions, hydrogen ions or oxygen gas may be generated at the electrode 111 and hydroxide ions or hydrogen gas may be generated at the electrode 121 due to the electrolysis of water. In addition, the active agent may cause a chemical reaction near the electrode 111 to change upon energization depending on the kind of the active agent. Furthermore, when the active agent solution reservoir 114 contains chlorine ions, this may cause chlorine gas or hypochlorous acid to be generated.

Similarly, when an active agent is an anionic active agent that dissociates into negative active agent ions, hydroxide ions or hydrogen gas may be generated at the electrode 111 and hydrogen ions or oxygen gas may be generated at the electrode 121 due to the electrolysis of water. In addition, the active agent may cause a chemical reaction near the electrode 111 to change upon energization depending on the kind of the active agent. Furthermore, when the electrolyte solution reservoir 122 contains chlorine ions, this may cause chlorine gas or hypochlorous acid to be generated.

If a gas is generated in the electrode assembly 110 or 120 as described above, energization from the electrode 111 or 121 to the active agent solution or the electrolyte solution may be inhibited. When hydrogen ions, hydroxide ions, or hypochlorous acid are generated in the electrode assembly 110 or 120, the ions and/or acid may be transferred to a biological interface. In addition, the alteration of an active agent may cause conditions such as the inability to obtain an initial active agent effect, and/or the production of toxic substances.

U.S. Pat. No. 4,744,787 discloses an iontophoresis device capable of addressing problems such as those described above. A silver electrode is used as an anode and a silver chloride electrode is used as a cathode.

An electrode reaction may preferentially occur in this iontophoresis device, where silver in the anode is oxidized to become insoluble silver chloride, while silver chloride is reduced at the cathode to become metallic silver. The generation of various gases and the production of various ions due to such electrode reactions as described above may thus be suppressed as a result.

However, it may be difficult to prevent dissolution of the silver electrode during storage of the iontophoresis device. In particular, the number of kinds of applicable active agents may be limited when the device is intended for administering a cationic active agent. In addition, the morphological change upon production of silver chloride from the silver electrode is large. Therefore, special consideration must be given in order to prevent morphological changes from affecting the properties of the device. As a result, certain restrictions may be imposed on the shape of the device (for example, it may not be possible to employ a laminate structure.) Furthermore, an active agent may be altered upon energization.

JP 3,040,517 B discloses an iontophoresis device shown in FIG. 10.

The iontophoresis device comprises an active electrode assembly 210 including an electrode 211, an electrolyte solution reservoir 212 that holds an electrolyte solution in contact with the electrode 211, an ion exchange membrane 213 of a second polarity, the ion exchange membrane 213 placed on the outer surface side of the electrolyte solution reservoir 212, an active agent solution reservoir 214 that holds an active agent solution containing an active agent ion of a first polarity, the active agent solution reservoir 214 placed on the outer surface side of the ion exchange membrane 213, and an ion exchange membrane 215 of the first polarity, the ion exchange membrane 215 placed on the outer surface side of the active agent solution reservoir 214; and a counter electrode assembly 220 and an electrode 230 similar to those shown in FIG. 9.

The electrolyte solution and the active agent solution are partitioned by the second ion exchange membrane 213 of the second polarity. As a result, the composition of the electrolyte solution can be selected independently of the active agent solution. An electrolyte solution that does not contain chlorine ions may be used, and an electrolyte having a lower oxidation or reduction potential than the electrolysis of water may be selected as the electrolyte in the electrolyte solution to suppress the production of oxygen gas, hydrogen gas, hydrogen ions, or hydroxide ions resulting from the electrolysis of water. Alternatively, the use of a buffer electrolyte solution into which a plurality of electrolytes are dissolved may suppress changes in pH due to the production of hydrogen ions or hydroxide ions. Furthermore, the transfer of an active agent ion to the electrolyte solution reservoir may be blocked by the second ion exchange membrane, helping to prevent changes in the active agent due to chemical reactions occurring upon energization.

The iontophoresis device disclosed in JP 3,040,517 has a large number of constitutive elements, and the electrolyte solution reservoir 212 and the active agent solution reservoir 214 must be handled in a wet state (a state where there is a high water content). A problem may thus arise in that automated production and/or mass production of the device may be difficult to achieve. In addition, production costs may not be reduced significantly.

BRIEF SUMMARY

In one aspect, the present disclosure is directed to an iontophoresis device comprising an electrode assembly that includes a polarizable electrode containing a conductive material having a capacitance per unit weight of 1 F/g or greater.

The iontophoresis device may include a polarizable electrode (also referred to as an electric double layer capacitor, "EDLC") containing a conductive material having a capacitance per unit weight of 1 F/g or greater. Accordingly, energization (electrical conduction) at the polarizable electrode is caused by the formation of an electrical double layer on the surface of the polarizable electrode.

Therefore, sufficient energization of the electrode for administering a desired quantity of active agent ions may be performed either without the occurrence of electrode reactions, or with a reduction in the amount electrode reactions occurring. As a result, the generation of gases such as oxygen gas, chlorine gas, and hydrogen gas, and the generation of ions such as hydrogen ions, and hydroxide ions, and the generation of hypochlorous acid may be reduced prevented.

The capacitance per unit weight of the conductor may be 10 F/g or greater. The amount of current available without causing an electrode reaction to occur may thus be increased.

In another aspect, the present disclosure is directed to an iontophoresis device comprising an electrode assembly including a polarizable electrode containing a conductor with a specific surface area of 10 $m^2$/g or greater.

The iontophoresis device may have a polarizable electrode containing a conductive material having a specific surface area of 10 $m^2$/g or greater. Accordingly, energization at the polarizable electrode is caused by the formation of an electrical double layer on the surface of the polarizable electrode. Therefore, sufficient energization of the electrode for administering a desired quantity of active agent ions may be performed either without the occurrence of electrode reactions, or with a reduction in the amount electrode reactions occurring. As a result, the generation of gases such as oxygen gas, chlorine gas, and hydrogen gas, and the generation of ions such as hydrogen ions, and hydroxide ions, and the generation of hypochlorous acid may be reduced prevented.

The specific surface area of the conductor may 100 $m^2$/g or greater. The amount of current available without causing an electrode reaction to occur may thus be increased.

It is possible to utilize a metallic conductor, such as gold, silver or stainless steel, or a non-metallic conductor, such as activated carbon or ruthenium oxide, as the conductive material. However, a non-metallic conductor may be advantageous as the conductive material because it may become possible to reduce or eliminate the possibility that metallic ions will elute from the polarizable electrode and be transferred to a subject. A similar effect may be obtained by utilizing a metallic conductor whose surface has been made insoluble by anodizing or the like.

In a further aspect, the present disclosure is directed to an iontophoresis device comprising an electrode assembly including a polarizable electrode containing activated carbon.

When using activated carbon, energization at the polarizable electrode is caused by forming an electrical double layer on the surface of activated carbon. Therefore, sufficient energization of the electrode for administering a desired quantity of active agent ions may be performed either without the occurrence of electrode reactions, or with a reduction in the amount electrode reactions occurring. As a result, the generation of gases such as oxygen gas, chlorine gas, and hydrogen gas, and the generation of ions such as hydrogen ions, and hydroxide ions, and the generation of hypochlorous acid may be reduced or prevented.

Normal activated carbon obtained by carbonizing and activating a raw material containing carbon such as coconut husk, wood flour, coal, pitch, or coke can be used as activated carbon to be incorporated into the polarizable electrode. The activated carbon may have a specific surface area of 10 $m^2$/g or greater. Alternatively the activated carbon may have a capacitance per unit weight of 1 F/g or greater.

Activated carbon fibers, which can be obtained by carbonizing and activating natural fiber or artificial fibers, may also be used. It therefore becomes possible to obtain a polarized electrode having superior handleability. Activated carbon fibers in the form of a woven fabric or a non-woven fabric may be used.

It may be advantageous to utilize an activated fiber obtained by carbonizing and activating novoloid fibers (fibers having a three dimensional molecular structure and obtained by attenuating a phenol fiber and then performing a cross linking treatment). It may thus become possible to obtain a polarizable electrode superior in flexibility or mechanical strength (e.g., tensile strength) and having a large specific surface area and high capacitance per unit weight.

The polarizable electrode may hold an electrolyte. A contact state between the polarizable electrode and the electrolyte may enhance conductivity from the polarizable electrode to the electrolyte.

A polarized electrode containing an activated carbon or an activated carbon fiber having superior permeability may be employed. The retention characteristics of the electrolyte, the handleability of the polarizable electrode, and the ease of fabrication of the device, may thus be enhanced by adjusting the viscosity of the electrolyte using a thickening agent.

The polarizable electrode may also be blended with a binder polymer.

Various binder polymers may be used without any particular limitations placed thereon provided that the binder polymer serves as a binder for the conductive material or the activated carbon and can impart chemically stable properties where the binder polymer is insoluble in solvents or the like.

For example, if a thermosetting resin such as a phenol resin is used as the binder polymer, it may be possible to configure the polarizable electrode by thermally setting the binder polymer in which the activated carbon is dispersed, or by thermally setting the binder polymer with which the activated carbon is impregnated. It may also be possible to increase the capacitance of the polarizable electrode by thermosetting the binder polymer in which the activated carbon is dispersed, or by thermally setting the binder polymer with which the activated carbon is impregnated, and thereafter carbonizing and activating the resultant.

In addition, flexibility may be imparted to the polarizable electrode by, for example, using a polymer having some degree of flexibility as the binder polymer. In this case, an iontophoresis device may include an electrode assembly having sufficient flexibility to follow the movements of a subject or the irregularities of the biological interface of the subject.

Polytetrafluoroethylene and polyvinylidene fluoride, for example, may be used for the binder polymer.

The typical loading of the binder polymer in the polarizable electrode containing activated carbon is 3 to 20 parts by weight with respect to 97 to 80 parts by weight of activated carbon.

The electrode assembly may further comprise a collector, with the polarized electrode placed on an outer surface side of the collector. Energization may thus occur from the polarizable electrode at a uniform current density. As a result, the iontophoresis device may be capable of administering an active agent with improved efficiency.

To attain this result, the collector may have a smaller resistivity or smaller surface resistance than that of the polarizable electrode.

The collector may be formed by using carbon fibers or carbon fiber paper.

The electrode assembly may therefore be formed without using metallic members. Metallic ions that may elute from metallic members and be transferred to a subject can thus be reduced or eliminated.

In addition, energization can occur from the polarizable electrode at a uniform current density because carbon fibers and carbon fiber paper have low surface resistances. An iontophoresis device including an electrode assembly having enough flexibility to conform to the movement of a subject or the irregularities of the biological interface of the subject may thus be provided because the carbon fibers and the carbon fiber paper are highly flexibility.

The polarized electrode may be blended with a binder polymer and the collector may be impregnated with a portion of the binder polymer.

A material that accepts impregnation with the binder polymer would be suitable. Carbon fibers or carbon fiber paper may be used for the collector to meet this requirement.

A portion of the conductive material or a portion of the activated carbon may enter into the collector along with the binder polymer when the collector is impregnated with the binder polymer.

If a thermosetting binder polymer is used, the binder polymer can be set after the collector has been impregnated with a composition comprising activated carbon and the binder polymer. Alternatively, the capacitance may be increased by further carbonizing and activating the resultant, after setting.

Polytetrafluoroethylene and polyvinylidene fluoride may be used for the binder polymer, as described above.

Collectors described in JP 2004-317317 A or JP 2005-222892 A by the applicant, each incorporated by reference herein in its entirety, may be employed as the collector.

A terminal member made of a conductive resin with carbon powder mixed in a polymer matrix may be attached to the conductive base material. Alternatively, the collector may comprise: a conductive sheet portion having a predetermined area; and an extension portion formed integrally with the conductive sheet portion.

A conductive paint or ink containing a conductive powder may be employed for the collector. Fabrication costs for the formation of the collector may thus be reduced.

In this case, a carbon powder may be used as the conductive powder contained in the conductive paint or ink. Metallic ions that may elute from metallic members and be transferred to a subject can thus be reduced or eliminated.

The collector and the polarized electrode may be bonded together by using a conductive adhesive.

The collector may be formed on a plastic substrate. Handleability of the collector may thus be enhanced without significant increases in fabrication costs. A film or thin plate of PET (polyethylene terephthalate) can be utilized as the plastic substrate.

An electrode assembly having a polarizable electrode can be used as an active electrode assembly or counter electrode assembly in an iontophoresis device.

An iontophoresis device typically includes an active electrode assembly that holds an active agent ion to be administered to a subject and a counter electrode assembly serving as a counter electrode of the active electrode assembly. The electrode assemblies described above may be used for the active electrode assembly and/or the counter electrode assembly in an iontophoresis device.

An active agent to be administered to a subject may be held by each assembly to be connected to an electric power source (in this case, each electrode assembly may serve as an active electrode assembly and/or a counter electrode assembly). A plurality of electrode assemblies may be connected to each polarity of an electric power source. Any of the electrode assemblies described above may be employed for any of the plurality of electrode assemblies.

The electrode assembly may further include an active agent solution reservoir that holds an active agent solution containing an active agent ion, the active agent solution reservoir being placed on the outer surface side of the polarizable electrode.

The polarity of the active agent ions may positive or negative. For convenience, the polarity of the active agent ions is referred to as a first polarity in the following description.

Active agent ions in the active agent solution reservoir may be administered to a subject by applying an electrical potential having the same polarity as that of the active agent ions to the polarizable electrode when the active agent solution reservoir is brought into contact with the biological interface of the subject.

In a case where the active agent solution reservoir is placed on an outer surface side of the polarizable electrode and the active agent solution in the active agent solution reservoir is in contact with the polarizable electrode, energization from the polarizable electrode to the active agent solution reservoir is partially or entirely due to the formation of an electrical double layer through the trapping of ions of a second polarity in the active agent solution reservoir into the polarizable electrode. Therefore, energization to an active agent solution can be performed while reducing or eliminating electrode reactions. As a result, the generation of a gas or of ions can be prevented or at least reduced.

When an electrolyte is held in the polarizable electrode, energization is caused mainly by the formation of an electrical double layer due to the trapping of an ion of a second polarity in the electrolyte and the energization from the electrolyte to the active agent solution is caused by the transfer of ions.

Energization can be performed by: causing the polarizable electrode to trap ions of the first polarity, in advance; bringing the active agent solution reservoir into contact with the biological interface of a subject in this trapped state; and applying an electrical potential of the first polarity to the polarizable electrode.

In this case, energization from the polarizable electrode to the active agent solution reservoir is entirely or partially caused by the transfer of the ions of the first polarity trapped in the polarizable electrode to the active agent solution held in the active agent solution reservoir (or to the electrolyte held in the polarizable electrode.) The generation of gases or of ions upon energization can therefore be prevented or at least reduced.

Ions of the first polarity can be trapped in the polarizable electrode through energization when an electrical potential of the second polarity is applied to the polarizable electrode. As a result, an active agent ion in the active agent solution (or other ions of the first polarity) can be trapped in the polarizable electrode.

The polarized electrode may hold an active agent solution having the same composition as that of the active agent solution in the active agent solution reservoir.

Conductivity from the polarizable electrode to the active agent solution may be enhanced by the increase of the contact area between the polarizable electrode and the active agent solution. In addition, changes over time in device properties due to mixing of the active agent solutions during storage of the device may be prevented because the active agent solutions held in the polarizable electrode and the active agent solution reservoir have the same composition.

The retention characteristics of the active agent solution in the polarizable electrode may be enhanced by blending the active agent solution held in the polarizable electrode with a thickener. In order to prevent changes over time in the device properties, the active agent solution in the active agent solution reservoir may be mixed with the same quantity of the same thickener as in the polarizable electrode.

An ion exchange membrane of the first polarity may be further placed on the outer surface side of the active agent solution reservoir. In this case, the transfer of a biological counter ion to the active agent solution reservoir may be blocked, the amount of a current consumed by the movement of the biological counter ion may be reduced, and the efficiency of administration of an active agent may be increased.

An ion exchange membrane of the second polarity may be further placed between the active agent solution reservoir and the polarizable electrode. In this case, even if an electrode reaction occurs to a certain extent, transfer of potentially harmful ions such as a hydrogen ions, hydroxide ions, or hypochlorous acid to a subject can be blocked by the ion exchange membrane of the second polarity. Further, transfer of altered active agent ions to a subject may be blocked by the ion exchange membrane of the second, even if the active agent ions are altered to a certain extent.

The second ion exchange membrane and the polarizable electrode may be joined integrally with each other. The integral joining may improve energization properties between the second ion exchange membrane and the polarizable electrode and simplify the assembly work of the electrode assembly. Therefore, automated production and/or mass production of the electrode assembly may be easily performed, and production costs may be reduced.

The second ion exchange membrane and the polarizable electrode can be joined together by using thermocompression bonding, for example.

The electrode assembly may further include a first ion exchange membrane doped with an active agent ion, the first ion exchange membrane being placed on an outer surface side of the polarized electrode.

The polarity of the first ion exchange membrane may be positive or negative. The polarity of the first ion exchange membrane is referred to as the first polarity in the following description.

In one or more embodiments, when the first ion exchange membrane is doped with an active agent ion of the first polarity (the active agent ions are bound to an ion exchange group in the first ion exchange membrane), ions of the first polarity are trapped in the polarizable electrode. When the first ion exchange membrane is brought into contact with the biological interface of a subject and an electrical potential of the first polarity is applied to the polarizable electrode, the active agent ions with which the first ion exchange membrane is doped are administered to the subject.

Energization from the polarizable electrode to the first ion exchange membrane is caused by the transfer of the ions of the first polarity trapped in the polarizable electrode to the first ion exchange membrane as a result of the release of ions. Therefore, the generation of gases or ions upon energization can be suppressed.

Without being restricted by theory, applicants believe that ions of the first polarity that transfer from the polarizable electrode exchange for the active agent ions with which the first ion exchange membrane is doped, allowing the active agent ions to be transferred to a subject.

The efficiency of administration of an active agent may increase because the first ion exchange membrane blocks the transfer of the biological counter ions. Furthermore, the efficiency of administration of the active agent ions may additionally increase because the active agent ions are held by the first ion exchange membrane that is brought into contact with the biological interface of a subject. In addition, the stability of the active agent ions during storage may improve, and the amount of stabilizers, antibacterial agents, antiseptics, or the like may be able to be reduced. In addition, the storage period of the device may be lengthened because the first ion exchange membrane holds the active agent ions.

Furthermore, it may be possible to configure an active electrode assembly only with the polarizable electrode and the first ion exchange membrane, without including wet members, such as an active agent solution reservoir, which has often been used in conventional iontophoresis devices. Assembly of the active electrode assembly may thus be simplified, automated production and/or mass production may be made easier, and production cost may be reduced.

The first ion exchange membrane may be placed in contact with the polarizable electrode to ensure the energization property between the polarizable electrode and the first ion exchange membrane.

The first ion exchange membrane and the polarizable electrode may be joined integrally together. The integral joining may improve energization properties between the first ion exchange membrane and the polarizable electrode and simplify assembly. Automated production and/or mass production may thus be made easier, and reductions in production costs may be achieved.

Doping of the first ion exchange membrane and trapping of the first polarity ions in the polarizable electrode may be performed by applying an electrical potential of the second polarity to the polarizable electrode for energization when the first ion exchange membrane is immersed in an active agent solution containing an appropriate concentration of active agent ions.

According to another embodiment, when an electrolyte solution reservoir that holds an electrolyte solution is placed between the polarizable electrode and the first ion exchange membrane is doped with an active agent ion of the first polarity, and the first ion exchange membrane is brought into contact with the biological interface of a subject, an electrical potential of the first polarity is applied to the polarizable electrode, thus delivering the active agent ions to the subject.

The electrolyte solution of the electrolyte solution reservoir in this case serves to supply ions of the first polarity ("first polarity electrolyte ions") to substitute for the active agent ions in the first ion exchange membrane and to supply an ion of the second polarity ("second polarity electrolyte ions") to be transferred to the polarizable electrode.

That is, the second polarity electrolyte ions transfer to the polarizable electrode and are trapped, thereby forming an electrical double layer. As a result, energization occurs from the polarizable electrode to the electrolyte solution reservoir.

In addition, the first polarity electrolyte ions substitute for the active agent ions in the first ion exchange membrane, allowing the active agent ions to be transferred to a subject with being restricted by theory.

As described above, energization from the polarizable electrode to the electrolyte solution reservoir is caused by the transfer of the second polarity electrolyte ions to the polarizable electrode. Therefore, the generation of gas or ions upon energization may be suppressed.

The second ion exchange membrane of the second polarity may be placed between the polarizable electrode and the electrolyte solution reservoir to block the transfer of the active agent ions to the polarizable electrode. Alteration of the active agent ions upon energization may thus be prevented.

The second ion exchange membrane and the polarizable electrode may be joined integrally together. The integral joining may achieve the effects similar to those described above.

Alternatively, the second ion exchange membrane of the second polarity may be placed between the electrolyte solution reservoir and the first ion exchange membrane to block the transfer of the active agent ions to the polarizable electrode. Alteration of the active agent ions upon energization may thus be prevented.

It should be noted that the second ion exchange membrane used should have a relatively low transport number (for example, a transport number of approximately 0.7 to approximately 0.95) because the first electrolytic ion cannot transfer to the first ion exchange membrane in order to substitute the active agent ions if the transport number of the second ion exchange membrane is 1. Use of a second ion exchange membrane having a relatively low transport number can sufficiently prevent the transfer of the active agent ions to the electrolyte solution reservoir.

The term "transport number" as used herein is defined as a ratio of a charge amount conveyed by the passage of an active agent counter ion through the second ion exchange membrane to the total charge conveyed through the second ion exchange membrane when an electrical potential of the first polarity is applied to the side of an electrolyte solution held by the electrolyte solution reservoir when the second ion exchange membrane is placed between the electrolyte solution and an active agent solution containing appropriate concentrations of active agent ions and active agent counter ion (for example, an active agent solution used for doping the first ion exchange membrane with the active agent ions).

In a yet further aspect, the present disclosure is directed to an iontophoresis device comprising: an active electrode assembly that holds an active agent ion; and a counter electrode assembly as a counter electrode of the active electrode assembly. The counter electrode assembly may comprise: a polarizable electrode containing a conductive material having a capacitance per unit weight of 1 F/g or greater, or having a specific surface area of 10 $m^2/g$ or greater, or activated carbon; and a third ion exchange membrane placed on the outer surface side of the polarizable electrode.

The polarity of the active agent ions may be positive or negative. The polarity of the active agent ions is referred to as the first polarity, and a polarizable electrode need not be employed. In addition, the active agent ions in the active electrode assembly may be held in an active agent solution and may be doped in an ion exchange membrane.

An ion exchange membrane of the first polarity or the second polarity may be used as the third ion exchange membrane.

If an ion exchange membrane of the first polarity is used as the third ion exchange membrane, an electrical potential of the first polarity maybe applied to the active electrode assembly to administer an active agent ion to a subject. In the counter electrode assembly, an electrical potential of the second polarity is applied to the polarizable electrode when the third ion exchange membrane is brought into contact with the biological interface of the subject.

Energization from the polarizable electrode to the third ion exchange membrane is caused by the formation of an electrical double layer due to the transfer of: ions of the first polarity bound to an ion exchange group of the third ion exchange membrane; or ions of the first polarity from the subject to the polarizable electrode and trapped therein. If the polarizable electrode holds an electrolyte, energization from the polarizable electrode to the third ion exchange membrane is caused mainly by the formation of an electrical double layer due to the transfer of ions of the first polarity in the electrolyte held in the polarizable electrode to the polarizable electrode and trapped therein. Therefore, the generation of gases and ions may be suppressed in the counter electrode assembly upon energization.

When an ion exchange membrane of the second polarity is used as the third ion exchange membrane, ions of the second polarity are trapped in the polarizable electrode of the counter electrode assembly in advance. An electrical potential of the first polarity is then applied to the active electrode assembly and an electrical potential of the second polarity is applied to the counter electrode assembly to administer an active agent ion to a subject.

Energization from the polarizable electrode to the third ion exchange membrane in the counter electrode assembly is thus caused by the transfer of the ions of the second polarity trapped in the polarizable electrode to the third ion exchange membrane as a result of the release of the ions. The generation of gasses and ions may thus be suppressed in the counter electrode assembly upon energization.

The ion of the second polarity can be trapped in the polarizable electrode by applying an electrical potential of the first polarity to the polarizable electrode of the counter electrode assembly when the third ion exchange membrane is immersed in an appropriate electrolyte solution.

Alternatively, it is also possible to use an ion exchange membrane of the second polarity as the third ion exchange membrane. The polarizable electrode may hold an electrolyte. In this case, energization from the polarizable electrode to the electrolyte is caused by the formation of an electrical double layer due to the trapping of an ion of the first polarity in the electrolyte held in the polarizable electrode to the polarizable electrode. Energization to a subject is caused by the transfer of an ion of the second polarity in the electrolyte held in the polarizable electrode to the subject, via the ion exchange membrane of second polarity.

The counter electrode assembly may have a simple configuration comprising only of the polarizable electrode and the third ion exchange membrane, and need not include any wet members, such as an electrolyte solution reservoir. Therefore, assembly of the counter electrode assembly can be simplified. Automated production and/or mass production of the electrode assembly may be easily performed. In addition, production cost reductions may be achieved.

The counter electrode assembly may include an electrolyte solution reservoir that holds an electrolyte solution in contact with the polarizable electrode instead of the third ion exchange membrane.

In this case, an electrical potential of the first polarity may be applied to the active electrode assembly to administer an active agent ion to a subject. In the counter electrode assembly, an electrical potential of the second polarity may be applied to the polarizable electrode when the electrolyte solution reservoir is brought into contact with the biological interface of the subject. Energization from the polarizable electrode to the electrolyte solution reservoir is caused by the formation of an electrical double layer due to the transfer of the first electrolytic ion of the electrolyte solution reservoir to the polarizable electrode to be trapped therein. Therefore, the generation of gases or ions in the counter electrode assembly upon energization may be suppressed.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
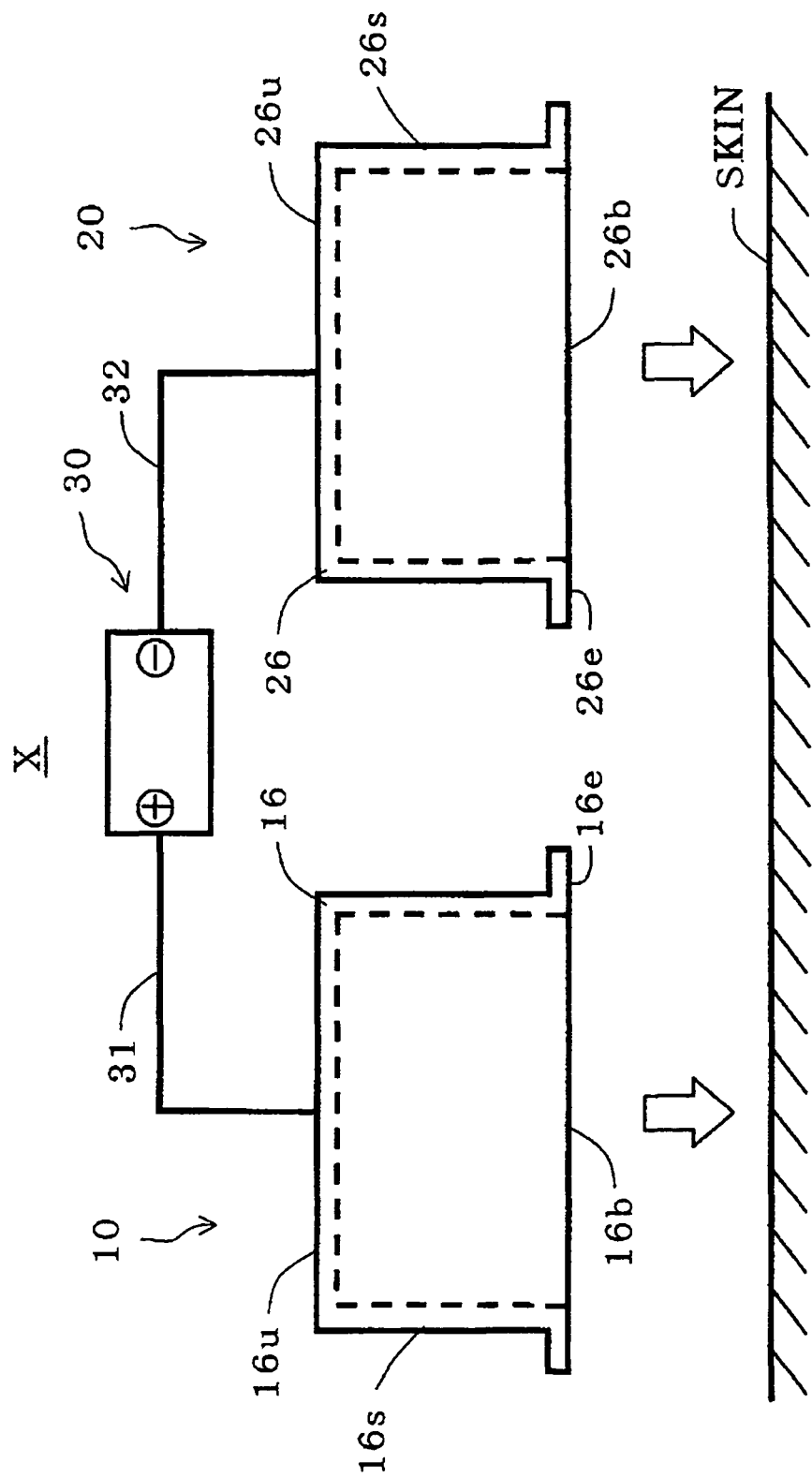
FIG. 1 is an explanatory view showing the schematic configuration of an iontophoresis device according to an embodiment.
Figure 2A:
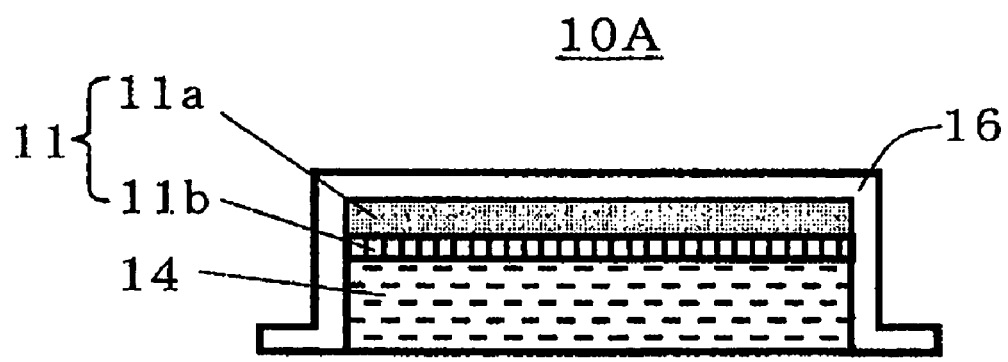
FIGS. 2A to 2D are explanatory sectional views each showing the configuration of an active electrode assembly of an iontophoresis device according to an embodiment.
Figure 2B:
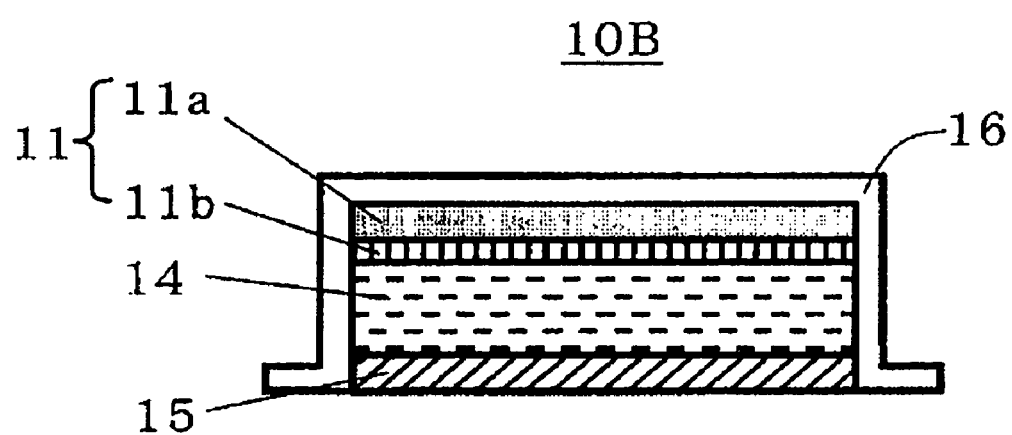
Figure 2C:
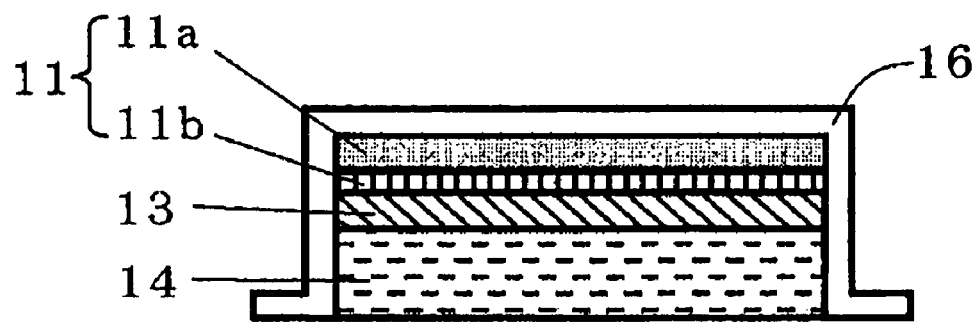
Figure 2D:
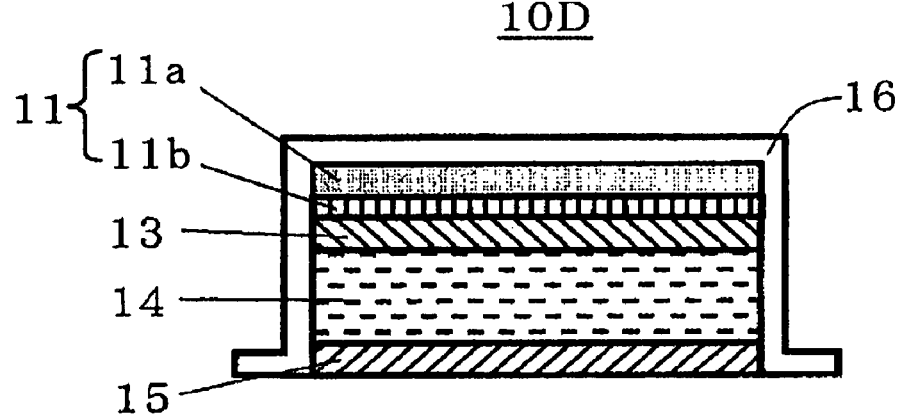

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well known structures associated with iontophoresis devices, controllers, voltage or current sources and/or membranes have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "another embodiment" means that a particular referent feature, structure, or characteristic described in connection with the embodiment is included in at least one embodiment. Thus, the appearances of the phrases "in one embodiment," or "in an embodiment," or "another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a system for evaluating an iontophoretic active agent delivery including "a controller" includes a single controller, or two or greater controllers. It should also be noted that the term "or" is generally employed in its sense including "and/or" unless the content clearly dictates otherwise.

As used herein the term "membrane" means a boundary, a layer, barrier, or material, which may, or may not be permeable. The term "membrane" may further refer to an interface. Unless specified otherwise, membranes may take the form a solid, liquid, or gel, and may or may not have a distinct lattice, non cross-linked structure, or cross-linked structure.

As used herein the term "ion selective membrane" means a membrane that is substantially selective to ions, passing certain ions while blocking passage of other ions. An ion selective membrane for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH and ACS also from Tokuyama Co., Ltd.

As used herein, the term "bipolar membrane" means a membrane that is selective to two different charges or polarities. Unless specified otherwise, a bipolar membrane may take the form of a unitary membrane structure, a multiple membrane structure, or a laminate. The unitary membrane structure may include a first portion including cation ion exchange materials or groups and a second portion opposed to the first portion, including anion ion exchange materials or groups. The multiple membrane structure (e.g., two film structure) may include a cation exchange membrane laminated or otherwise coupled to an anion exchange membrane. The cation and anion exchange membranes initially start as distinct structures, and may or may not retain their distinctiveness in the structure of the resulting bipolar membrane.

As used herein, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules a first rate, and some other molecules a second rate different than the first. In yet further embodiments, the "semi-permeable membrane" may take the form of a selectively permeable membrane allowing only certain selective molecules to pass through it.

As used herein, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three dimensional network, a colloidal suspension of a liquid in a solid, a semi-solid, a cross-linked gel, a non cross-linked gel, a jelly-like state, and the like. In some embodiments, the gel matrix may result from a three dimensional network of entangled macromolecules (e.g., cylindrical micelles). In some embodiment a gel matrix may include hydrogels, organogels, and the like. Hydrogels refer to three-dimensional network of, for example, cross-linked hydrophilic polymers in the form of a gel and substantially comprising water. Hydrogels may have a net positive or negative charge, or may be neutral.

A used herein, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

A used herein, the term "active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., an active agent, a therapeutic compound, pharmaceutical salts, and the like) non-pharmaceuticals (e.g., cosmetic substance, and the like), a vaccine, an immunological agent, a local or general anesthetic or painkiller, an antigen or a protein or peptide such as insulin, a chemotherapy agent, an anti-tumor agent. In some embodiments, the term "active agent" further refers to the active agent, as well as its pharmacologically active salts, pharmaceutically acceptable salts, proactive agents, metabolites, analogs, and the like. In some further embodiment, the active agent includes at least one ionic, cationic, ionizeable and/or neutral therapeutic active agent and/or pharmaceutical acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. While other active agents may be polarized or polarizable, that is exhibiting a polarity at one portion relative to another portion. For instance, an active agent having an amino group can typically take the form an ammonium salt in solid state and dissociates into a free ammonium ion ($NH_4^+$) in an aqueous medium of appropriate pH. The term "active agent" may also refer to neutral agents, molecules, or compounds capable of being delivered via electro-osmotic flow. The neutral agents are typically carried by the flow of, for example, a solvent during electrophoresis. Selection of the suitable active agents is therefore within the knowledge of one skilled in the art.

Non-limiting examples of such active agents include lidocaine, articaine, and others of the -caine class; morphine, hydromorphone, fentanyl, oxycodone, hydrocodone, buprenorphine, methadone, and similar opioid agonists; sumatriptan succinate, zolmitriptan, naratriptan HCl, rizatriptan benzoate, almotriptan malate, frovatriptan succinate and other 5-hydroxytryptamine 1 receptor subtype agonists; resiquimod, imiquidmod, and similar TLR 7 and 8 agonists and antagonists; domperidone, granisetron hydrochloride, ondansetron and such anti-emetic active agents; zolpidem tartrate and similar sleep inducing agents; L-dopa and other anti-Parkinson's medications; aripiprazole, olanzapine, quetiapine, risperidone, clozapine and ziprasidone as well as other neuroleptica; diabetes active agents such as exenatide; as well as peptides and proteins for treatment of obesity and other maladies.

As used herein and in the claims, the term "subject" generally refers to any host, animal, vertebrate, or invertebrate, and includes fish, mammals, amphibians, reptiles, birds, and particularly humans.

The headings provided herein are for convenience only and do not interpret the scope or meaning of the embodiments.

FIG. 1 is an explanatory view showing the schematic configuration of an iontophoresis device X.

An iontophoresis device for administering an active agent whose active agent component dissociates into positive active agent ions (for example, lidocaine hydrochloride or morphine hydrochloride) is exemplified below. An iontophoresis device for administering an active agent whose active agent component dissociates into negative ions (for example, ascorbic acid), can be configured by reversing the polarity of each member and electric potential having a polarity described below.

Referring to FIG. 1, the iontophoresis device X comprises: an electric power source 30; an active electrode assembly 10 connected to the positive pole of the electric power source 30 with an electric supply line 31; and a counter electrode assembly 20 connected to the negative pole of the electric power source 30 with an electric supply line 32.

The active electrode assembly 10 comprises a container 16 that includes an upper wall 16u and an outer peripheral wall 16s. The counter electrode assembly 20 comprises a container 26 that includes an upper wall 26u and an outer peripheral wall 26s. A space capable of housing various structures to be described later is formed in the container 16 and in the container 26. Lower or outer portions 16b and 26b of the containers 16 26 are open.

The container 16 and the container 26 can each be formed of a variety of materials, such as a plastic, and may be formed of a flexible material capable of: preventing the evaporation of water from the inside of the container and the penetration of foreign matter from the outside; and following the movement of a subject or the irregularities of the biological interface of the subject. In addition, a removable liner comprising an appropriate material for preventing the evaporation of water and the mixing of foreign matter during storage of the iontophoresis device X may be applied to the lower portions 16b or 26b of the containers 16 and 26, respectively. An adhesive layer for improving adhesiveness to a biological interface upon administration of an active agent may be arranged on a lower end portion 16e or 26e of the outer peripheral wall 16s or 26s, respectively.

The containers 16 and 26 are not necessarily arranged in the absence of a wet member such as an active agent solution reservoir or an electrolyte solution reservoir (a member with a high water content) like active electrode assemblies 10H and 10I and counter electrode assemblies 20A to 20C to be described later.

A battery, a constant voltage device, a constant current device, a constant voltage/current device, or the like can be used as the electric power source 30. A constant current device whose current can be adjusted in the range of approximately 0.01 to 1.0 mA/cm$^2$, or in the range of approximately 0.01 to 0.5 mA/cm$^2$, and which operates under safe voltage conditions, specifically at approximately 50 V or less, or at 30 V or less, may be used.

FIGS. 2A to 2D are explanatory sectional views showing the configurations of active electrode assemblies 10A to 10D each of which can be used as the active electrode assembly 10 of the iontophoresis device X.

The active electrode assembly 10A has an electrode member 11 comprising a conductive collector 11a connected to the electric supply line 31 and a polarizable electrode 11b formed on the outer surface side of the collector 11a. For the polarizable electrode 11b, a member having, for example, a planer shape and containing any one of a conductive material having a capacitance per unit weight of 1 F/g or greater, a conductive material having a specific surface area of 10 m$^2$/g or greater, and activated carbon can be used.

The polarizable electrode 11b may be obtained by forming, for example, a composition prepared by blending 95 parts by weight of activated carbon powder having a specific surface area of about 100 m2/g with 5 parts by weight of polytetrafluoroethylene into a membrane shape.

The polarizable electrode 11b can be configured from activated carbon fiber or an activated carbon fiber impregnated with a binder polymer. Activated fibers may be obtained by carbonizing and activating novoloid fibers having a extremely large specific surface area (for example, 1000 to 2500 m$^2$/g), high tensile strength (for example, 300 to 400 N/mm$^2$), superior flexibility. Activated fibers obtained by carbonizing and activating novoloid fiber are publicly available, for example, as "Kynol activated carbon fiber" from Nippon Kynol Inc.

The polarizable electrode 11b in the active electrode assembly 10A can be impregnated with an electrolyte to hold the electrolyte. The polarizable electrode 11b may hold an active agent solution having the same composition as the active agent solution held in the active agent solution reservoir 14 mentioned later.

The polarizable electrode 11b may be stacked integrally on the collector 11a by using an approach such as thermocompression bonding or adhesion using a conductive adhesive.

The thickness of the polarizable electrode 11b can be from about 10 µm to 20 mm.

The active electrode assembly 10A may include an active agent solution reservoir 14 that holds an active agent solution in contact with polarizable electrode 11b. The active agent solution is a solution of an active agent whose active agent component dissociates into positive active agent ions. The active agent solution reservoir 14 can hold the active agent solution in a liquid state, or can hold the active agent solution by impregnating an appropriate absorbing carrier such as gauze, filter paper, or a gel matrix with the active agent solution.

In the active electrode assembly 10A, a positive voltage is applied to the collector 11a when the active agent solution reservoir 14 is brought into contact with the biological interface of a subject. An active agent ion in the active agent solution reservoir 14 is thus administered to the subject. Energization from the polarizable electrode 11 to the active agent solution reservoir 14 is caused by the formation of an electrical double layer due to the trapping of negative ions in the active agent solution into the polarizable electrode 11b. (If the polarizable electrode 11b holds an electrolyte, energization at the polarizable electrode is also caused by the trapping of negative ions in the electrolyte to the polarizable electrode 11b). The generation of oxygen gas, chlorine gas, hydrogen ions, and/or hypochlorous acid due to energization can therefore be suppressed.

The active electrode assembly 10B comprises: the electrode member 11 and the active agent solution reservoir 14 identical or similar to those of the active electrode assembly 10A; and a cation exchange membrane 15 placed on the outer surface side of the active agent solution reservoir 14.

The active electrode assembly 10B is similar to the active electrode assembly 10A with respect to suppression of the generation of gases and ions upon energization. In addition, the active electrode assembly 10B may be more efficient in administration of an active agent ion because the transfer of a biological counter ion to the active agent solution reservoir 14 is blocked by the cation exchange membrane 15.

The active electrode assembly 10C comprises: the electrode member 11 and the active agent solution reservoir 14 identical or similar to those of the active electrode assembly 10A; and an anion exchange membrane 13 placed between the polarizable electrode 11b and the active agent solution reservoir 14.

In the active electrode assembly 10C, energization from the polarizable electrode 11 to the active agent solution reservoir 14 is caused by the formation of an electrical double layer due to the transfer of negative ions in the active agent solution reservoir 14 to the polarizable electrode 11b via the anion exchange membrane 13 to be trapped in the layer. (If the polarizable electrode 11b holds an electrolyte, energization at the polarizable electrode 11b is also caused by the trapping of negative ions in the electrolyte into the polarizable electrode 11b, in addition to the above.) Therefore, the active electrode assembly 10C is similar to the active electrode assembly 10A regarding the suppression of the generation of gases and ions upon energization.

Furthermore, the active electrode assembly 10C may prevent decomposition and/or alteration of an active agent upon energization because the transfer of an active agent ion in the active agent solution reservoir 14 to the side of the polarizable electrode 11b is blocked by the anion exchange membrane 13.

The active electrode assembly 10D comprises: the electrode member 11 and the active agent solution reservoir 14 identical or similar to those of the active electrode assembly 10A; the anion exchange membrane 13 placed between the polarizable electrode 11b and the active agent solution reservoir 14; and the cation exchange membrane 15 placed on the outer surface side of the active agent solution reservoir 14.

The active electrode assembly 10D is similar to the active electrode assembly 10A regarding the suppression of the generation of a gas or of ions upon energization. The active electrode assembly 10D may prevention decomposition and/or alteration of an active agent upon energization, and may increase the efficiency of administration of the active agent, similar to the electrode assemblies 10B and 10C.

In the active electrode assemblies 10C and 10D, the polarizable electrode 11b and the anion exchange membrane 13 can be joined and integrated together by using an approach such as thermocompression bonding. This action can improve a state of energization from the polarizable electrode 11b to the anion exchange membrane 13 or simplify the assembly work of each of the active electrode assemblies 10C and 10D.

Figure 3A:
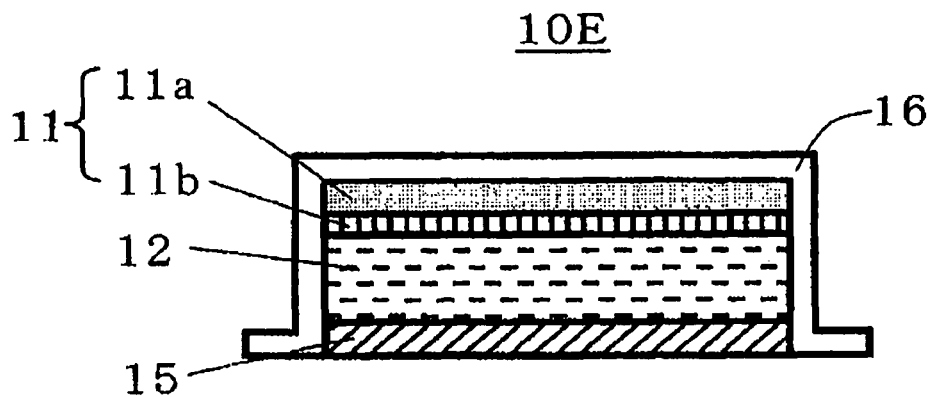
FIGS. 3A to 3C are explanatory sectional views each showing the configuration of an active electrode assembly of an iontophoresis device according to an embodiment.
Figure 3B:
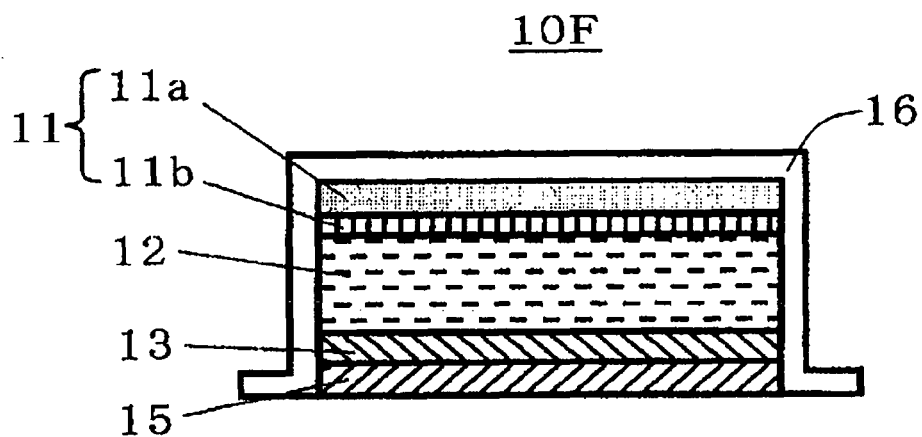
Figure 3C:
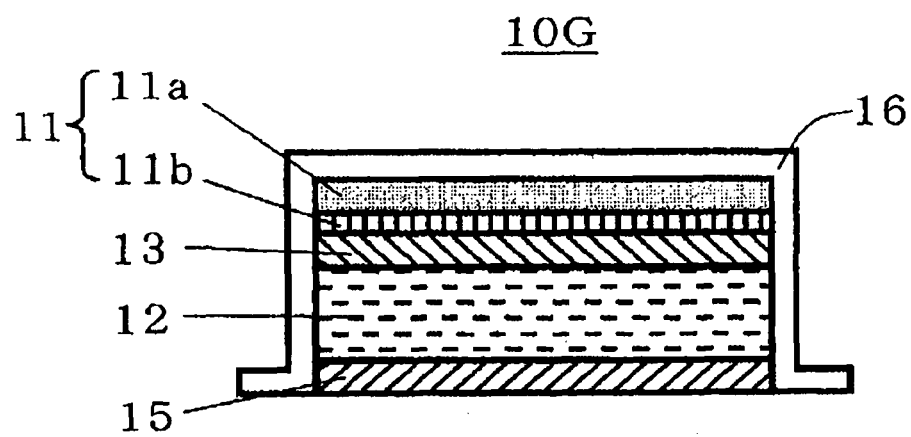

FIGS. 3A to 3C are explanatory sectional views showing the configurations of active electrode assemblies 10E to 10G according to another aspect each of which can be used as the active electrode assembly 10 of the iontophoresis device X.

The active electrode assembly 10E comprises: the electrode member 11 identical or similar to that of the active electrode assembly 10A; an electrolyte solution reservoir 12 that holds an electrolyte solution in contact with the polarizable electrode 11b; and the cation exchange membrane 15 placed on the outer surface side of the electrolyte solution reservoir 12 and doped with a positive active agent ions.

In the active electrode assembly 10E, a positive voltage may be applied to the collector 11a when the cation exchange membrane 15 is brought into contact with the biological interface of a subject, whereby the active agent ions with which the cation exchange membrane 15 is doped are administered to the subject.

Energization from the polarizable electrode 11b to the electrolyte solution reservoir 12 is caused by the formation of an electrical double layer due to the transfer of negative ions in the electrolyte solution to the polarizable electrode 11b to be trapped therein. Therefore, the generation of oxygen gas, chlorine gas, hydrogen ions, and hypochlorous acid due to energization can be suppressed.

Energization from the electrolyte solution reservoir 12 to the cation exchange membrane 15 is caused by the transfer of positive ions in the electrolyte solution reservoir 12 to the cation exchange membrane 15. The positive ions may substitute for an active agent ion that has transferred to a subject, binding to ion exchange groups in the cation exchange membrane 15.

An active agent can be administered efficiently in the active electrode assembly 10E because the cation exchange membrane 15 blocks the transfer of a biological counter ion to the electrolyte solution reservoir 12.

The electrolyte solution reservoir 12 of the active electrode assembly 10E may hold the electrolyte solution in a liquid state, or may hold the electrolyte solution by impregnating an absorbing carrier such as gauze, filter paper, or a gel matrix with the electrolyte solution.

When a positive ion in the electrolyte solution reservoir 12 has a mobility larger than that of an active agent ion, the transfer of the positive ion to a subject occurs preferentially, so the efficiency of administration of an active agent may drop. Therefore, the electrolyte solution of the electrolyte solution reservoir 12 is preferably free of positive ions having a mobility comparable to or larger than that of an active agent ion.

The cation exchange membrane 15 can be doped with an active agent ion by immersing the cation exchange membrane 15 in an active agent solution containing an appropriate concentration of active agent ions. The amount of the active agent ions with which the membrane is to be doped at this time can be adjusted depending on, for example, the concentration of the active agent ions in the active agent solution, an immersion time, and the number of times of immersion.

The active electrode assembly 10F comprises: the electrode member 11, the electrolyte solution reservoir 12, and the cation exchange membrane 15 identical or similar to those of the active electrode assembly 10E; and the anion exchange membrane 13 placed between the electrolyte solution reservoir 12 and the cation exchange membrane 15.

The active electrode assembly 10F is similar to the active electrode assembly 10E regarding the suppression of the generation of gases and ions upon energization. The active electrode assembly 10F also may prevent alteration of an active agent near the polarizable electrode 11b upon energization because the transfer of the active agent ions with which the cation exchange membrane 15 is doped to the electrolyte solution reservoir 12 is blocked by the anion exchange membrane 13.

For energization from the electrolyte solution reservoir 12 to the cation exchange membrane 15 in the active electrode assembly 10F, positive ions in the electrolyte solution reservoir 12 should pass through the anion exchange membrane 13 to transfer to the cation exchange membrane 15. Therefore, an anion exchange membrane having a relatively low transport number is used for the anion exchange membrane 13.

The electrolysis of water occurs at an interface between the anion exchange membrane 13 and the cation exchange membrane 15 in some cases depending on energization conditions. Therefore, a semi-permeable membrane capable of permitting the passage of a positive ion in the electrolyte solution reservoir 12 may be further placed between the anion exchange membrane 13 and the cation exchange membrane 15 to prevent electrolysis.

The interface between the anion exchange membrane 13 and the cation exchange membrane 15 or each interface among the anion exchange membrane 13, the semi-permeable membrane, and the cation exchange membrane 15 can be joined by using an approach such as thermocompression bonding or via irradiation. This may improve energization properties and handleability.

The anion exchange membrane 13 in the active electrode assembly 10F permits the passage of positive ions in the electrolyte solution reservoir 12. Meanwhile, similar characteristics as those described above may be obtained if the membrane is replaced with a semi-permeable membrane having a molecular weight cutoff property to block the passage of active agent ions.

The active electrode assembly 10G comprises: the electrode member 11, the electrolyte solution reservoir 12, and the cation exchange membrane 15 identical or similar to those of the active electrode assembly 10E; and the anion exchange membrane 13 placed between the polarizable electrode 11 and the electrolyte solution reservoir 12.

In the active electrode assembly 10G, energization from the polarizable electrode 11b to the electrolyte solution reservoir 12 is caused by the formation of an electrical double layer due to the transfer of negative ions in the electrolyte solution reservoir 12 to the polarizable electrode 11b via the anion exchange membrane 13 to be trapped in the layer. Therefore, the active electrode assembly 10G is similar to the active electrode assembly 10E regarding the suppression of the generation of gases and ions upon energization.

Energization from the electrolyte solution reservoir 12 to the cation exchange membrane 15 occurs in the same manner as in the case of the active electrode assembly 10E. Furthermore, decomposition and alteration of an active agent upon energization may be prevented because the transfer of the active agent ions with which the cation exchange membrane 15 is doped to the polarizable electrode 11 is blocked by the anion exchange membrane 13.

Figure 4A:
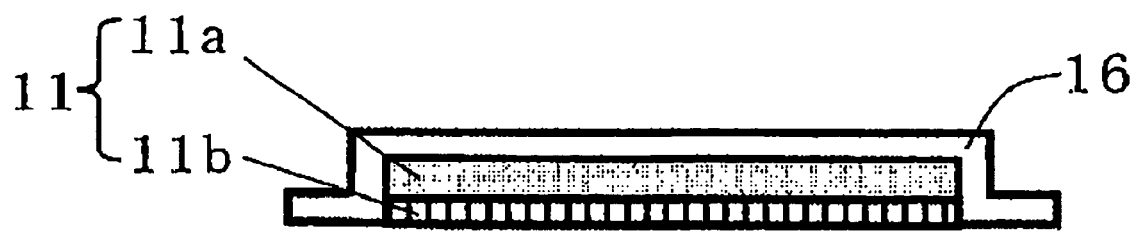
FIGS. 4A and 4B are explanatory sectional views each showing the configuration of an active electrode assembly of an iontophoresis device according to an embodiment.
Figure 4B:
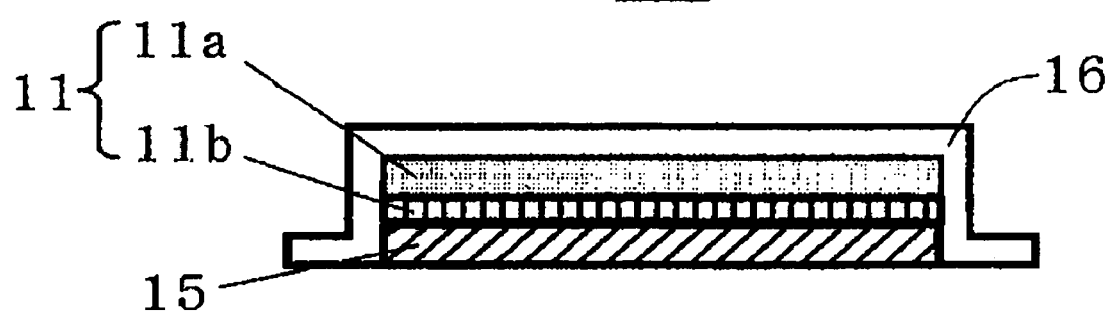
Figure 5A:
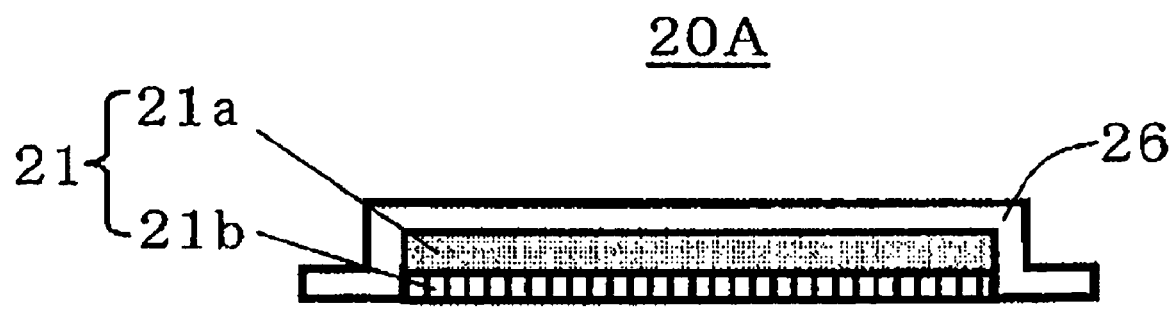
FIGS. 5A to 5D are explanatory sectional views each showing the configuration of a counter electrode assembly of an iontophoresis device according to an embodiment.
Figure 5B:
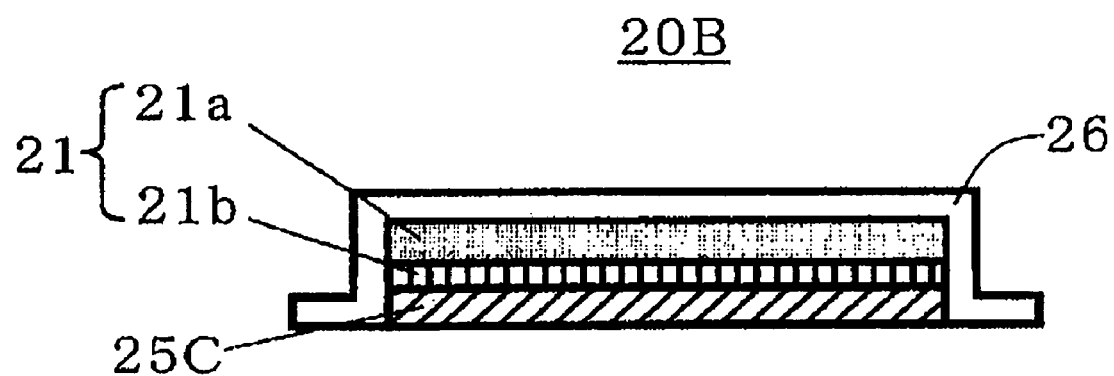
Figure 5C:
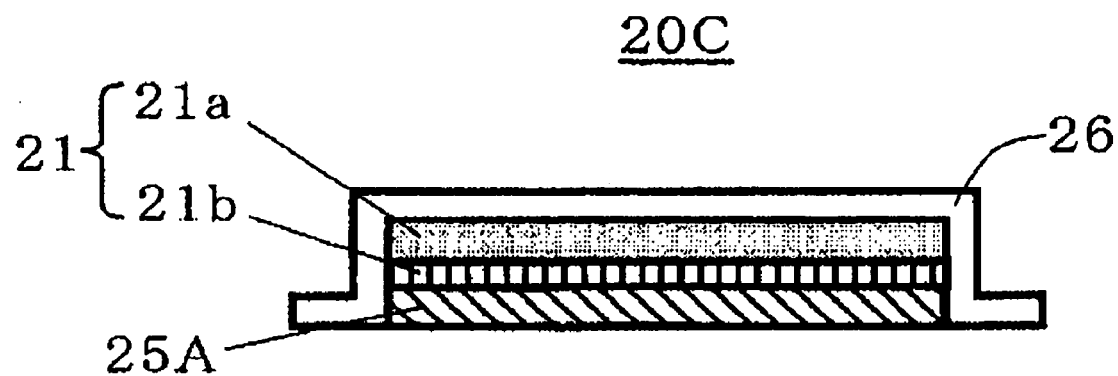
Figure 5D:
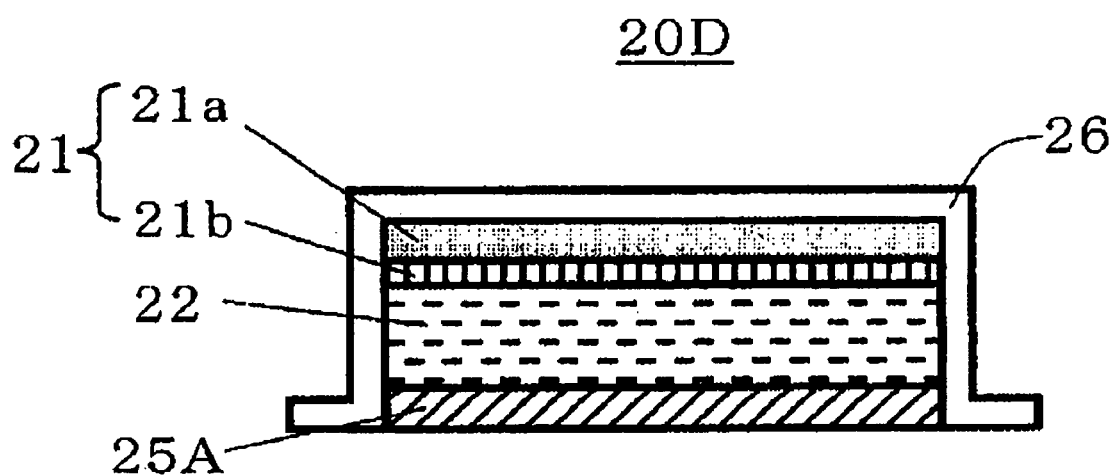

FIGS. 4A and 4B are explanatory sectional views showing the configurations of active electrode assemblies 10H and 10I, each of which can be used as the active electrode assembly 10 of the iontophoresis device X.

The active electrode assembly 10H is configured by the same electrode member 11 as that of the active electrode assembly 10A.

In the active electrode assembly 10H, a treatment for trapping an active agent ion into the polarizable electrode 11b is performed in advance before an active agent is administered.

This treatment can be performed through energization by applying a negative voltage to the collector 11a when the polarizable electrode 11b is immersed in an active agent solution containing an appropriate concentration of active agent ions.

The active electrode assembly 10H that has been subjected to the above treatment may be used to apply a positive voltage to the collector 11a when the polarizable electrode 11b is brought into contact with the biological interface of a subject, whereby the active agent ions with which the polarizable electrode 11b is doped is administered to the subject.

In this case, energization from the polarizable electrode 11b to the biological interface of the subject is caused by the transfer of the active agent ions trapped in the polarizable electrode 11b to the biological interface of the subject as a result of the release of the ion. Therefore, the generation of oxygen gas, chlorine gas, hydrogen ions or hypochlorous acid due to energization may be suppressed.

In the active electrode assembly 10H, it is also possible to impregnate the polarizable electrode 11b with an active agent solution. Treatment for trapping positive ions in the polarizable electrode 11b thus becomes unnecessary. That is, energization from the polarizable electrode 11b to the biological interface of a subject is caused by the trapping of a negative ion in the active agent solution into the polarizable electrode 11b and by the transfer of the active agent ions in the active agent solution to the biological interface of the subject. Therefore, the generation of an oxygen gas or a chlorine gas or of a hydrogen ion or hypochlorous acid due to energization may be suppressed.

The active electrode assembly 10H has an extremely simple structure comprising only of the collector 11a and the polarizable electrode 11b. Therefore, automated production and/or mass production of the active electrode assembly 10H can be performed easily. In addition, production costs 10H can be reduced.

The active electrode assembly 10I comprises: the electrode member 11 identical to that of the active electrode assembly 10A; and the cation exchange membrane 15 placed on the outer surface side of the polarizable electrode 11b so as to be in contact with the layer.

In the active electrode assembly 10I, a treatment for doping the cation exchange membrane 15 with an active agent ion and a treatment for trapping positive ions into the polarizable electrode 11b are performed in advance before an active agent is administered.

This treatment can be performed through energization by applying a negative voltage to the collector 11a when the cation exchange membrane 15 is immersed in an active agent solution containing an appropriate concentration of active agent ions. Prior to the treatment, the cation exchange membrane 15 may be doped with the active agent ions in the same manner as that described above with respect to the active electrode assembly 10E.

The active electrode assembly 10I that has been subjected to the above treatment may be used to apply a positive voltage to the collector 11a when the cation exchange membrane 15 is brought into contact with the biological interface of a subject, whereby the active agent ions with which the cation exchange membrane 15 is doped is administered to the subject.

In this case, energization from the polarizable electrode 11b to the cation exchange membrane 15 occurs due to the transfer of the positive ions trapped in the polarizable electrode 11b to the cation exchange membrane 15 as a result of the release of ions. Therefore, the generation of oxygen gas, chlorine gas, hydrogen ions, and hypochlorous acid due to energization may be suppressed. Without being limited by theory, applicants believe that the positive ions that transfer from the polarizable electrode 11b to the cation exchange membrane 15 may substitute for active agent ions that transfer to the subject, to thereby bind to an ion exchange group in the cation exchange membrane 15.

In the active electrode assembly 10I, it is also possible to impregnate the polarizable electrode 11b with an active agent solution or an electrolyte. In this case, the treatment for trapping positive ions into the polarizable electrode 11b becomes unnecessary. That is, in this case, energization from the polarizable electrode 11b to the ion exchange membrane 15 is caused by the trapping of negative ions in the active agent solution or the electrolyte into the polarizable electrode 11b and by the transfer of positive ions in the active agent solution or the electrolyte to the ion exchange membrane 15. Therefore, the generation of an oxygen gas or a chlorine gas or of a hydrogen ion or hypochlorous acid due to energization may be suppressed.

As shown in the figure, the active electrode assembly 10I has a simple structure comprising only of the collector 11a, the polarizable electrode 11b and the cation exchange membrane 15, and there is no need to use a wet member upon assembly of the active electrode assembly 10I. Therefore, automated production and/or mass production of the active electrode assembly 10I can be performed easily. In addition, production costs 10I can be reduced.

The polarizable electrode 11b and the cation exchange membrane 15 may be joined and integrated with each other by using an approach such as thermocompression bonding or irradiation, whereby energization property between them and the handleability of them can be improved.

FIGS. 5A to 5D are explanatory sectional views showing the configurations of counter electrode assemblies 20A to 20D each of which can be used as the counter electrode assembly 20 of the iontophoresis device X.

The counter electrode assembly 20A comprises an electrode member 21 having a collector 21a connected to the electric supply line 32 and a polarizable electrode 21b formed on the collector 21a. The polarizable electrode 21b has substantially the same configuration as that of the polarizable electrode 11b of the active electrode assembly 10A That is, the polarizable electrode 21b may comprise a member having, for example, a planer shape and containing any one of a conductive material having a capacitance per unit weight of 1 F/g or greater, a conductive material having a specific surface area of 10 $m^2$/g or greater, and activated carbon.

The polarizable electrode 21b may be obtained by forming, for example, a composition, which is prepared by blending 95 parts by weight of activated carbon powder having a specific surface area of about 100 m²/g with 5 parts by weight of polytetrafluoroethylene, into a membrane shape. The polarizable electrode 21b may comprise an activated carbon fiber obtained by carbonizing and activating a novolid fiber.

It is possible to impregnate the polarizable electrode 21b with an electrolyte.

In the counter electrode assembly 20A, a negative voltage is applied to the collector 21a when the polarizable electrode 21b is brought into contact with a subject. Thus, a positive ion transfers from the biological interface of the subject or the electrolyte held in the polarizable electrode 21b to the polarizable electrode 21b to be trapped in the layer, whereby an electrical double layer is formed to cause energization. Therefore, the generation of hydrogen gas and hydroxide ions upon energization is suppressed.

If negative ions are trapped in advance into the polarizable electrode 21b, the negative ions transfer to a subject to cause energization. The generation of hydrogen gas and hydroxide ion upon energization is also suppressed in this case.

The counter electrode assembly 20A has a simple structure comprising only of the collector 11a and the polarizable electrode 11b. Therefore, automated production and/or mass production of the active electrode assembly 20A can be performed easily. In addition, production costs can be reduced. In 20 addition, the counter electrode assembly 20A has the same configuration as that of the active electrode assembly 10H, so the counter electrode assembly 20A and the active electrode assembly 10H can be produced by using the same processes. Accordingly, the production process of an iontophoresis device including the counter electrode assembly 20A and the active electrode assembly 10H can be further simplified. In addition, automated production and/or mass production of the iontophoresis device can be easily performed, and the production costs of the iontophoresis device can be reduced.

The counter electrode assembly 20B has the electrode member 21 identical or similar to that of the counter electrode assembly 20A and a cation exchange membrane 25C placed in contact with the polarizable electrode 21b.

In the counter electrode assembly 20B, a negative voltage is applied to the collector 21a when the cation exchange membrane 25C is brought into contact with a subject. As a result, energization occurs due to the formation of an electrical double layer due to the transfer of positive ions from the biological interface of the subject or the electrolyte held in the polarizable electrode 21b to the polarizable electrode 21b via the cation exchange membrane 25C to be trapped in the layer. Therefore, the generation of hydrogen gases and hydroxide ions upon energization may be suppressed.

The counter electrode assembly 20B has a simple structure comprising only of the collector 21a, polarizable electrode 21b and the cation exchange membrane 25C and having no wet member. Therefore, automated production and/or mass production of the active electrode assembly 20B can be performed easily. In addition, production costs 20B can be reduced. In addition, the counter electrode assembly 20B has the same configuration as that of the active electrode assembly 10I, so the counter electrode assembly 20B and the active electrode assembly 10I can be produced by using the same process. Accordingly, the production process of an iontophoresis device including the counter electrode assembly 20B and the active electrode assembly 10I can be further simplified. In addition, the automated production and/or mass production of the iontophoresis device can be easily performed, and production costs for the iontophoresis device can be reduced.

The counter electrode assembly 20C has the electrode member 21 identical to that of the counter electrode assembly 20A and an anion exchange membrane 25A placed so as to be in contact with the polarizable electrode 21b.

In the counter electrode assembly 20C, a treatment for trapping a negative ion into the polarizable electrode 21b is performed in advance before energization for administering an active agent is performed.

This treatment for trapping can be performed through energization by applying a positive voltage to the polarizable electrode 21 when the anion exchange membrane 25A is immersed in an appropriate electrolyte solution.

Upon administration of an active agent, a negative voltage is applied to the polarizable electrode 21 when the anion exchange membrane 25A of the counter electrode assembly 20B that has been subjected to the above treatment is brought into contact with the biological interface of a subject.

In this case, energization from the polarizable electrode 21 to the biological interface of the subject is caused by the transfer of the negative ions trapped in the polarizable electrode 21b to the biological interface of the subject as a result of the release of the ions. Therefore, the generation of oxygen gases and hydroxide ions is suppressed.

The counter electrode assembly 20C has a simple structure having no wet members, similar to the counter electrode assembly 20B. Therefore, automated production and/or mass production of the active electrode assembly 20C can be performed easily. In addition, production costs 20C can be reduced.

The counter electrode assembly 20D comprises: the electrode member 21 identical to that of the counter electrode assembly 20A; an electrolyte solution reservoir 22 that holds an electrolyte solution in contact with the polarizable electrode 21b; and the anion exchange membrane 25A placed on the outer surface side of the electrolyte solution reservoir 22.

In the counter electrode assembly 20D, a negative voltage is applied to the collector 21a when the anion exchange membrane 25A is brought into contact with a subject, energization is caused by the formation of an electrical double layer due to the transfer of a positive ion in the electrolyte solution reservoir 22 to the polarizable electrode 21b to be trapped in activated carbon. Therefore, the generation of hydrogen gas and hydroxide ions upon energization may be suppressed.

Energization between the electrolyte solution reservoir 22 and the biological interface of the subject is mainly due to the transfer of negative ions in the electrolyte solution reservoir 22 to the subject via the anion exchange membrane 25A.

The counter electrode assembly 20D may achieve similar effects as that described above even when the anion exchange membrane 25A is omitted.

Figure 6A:
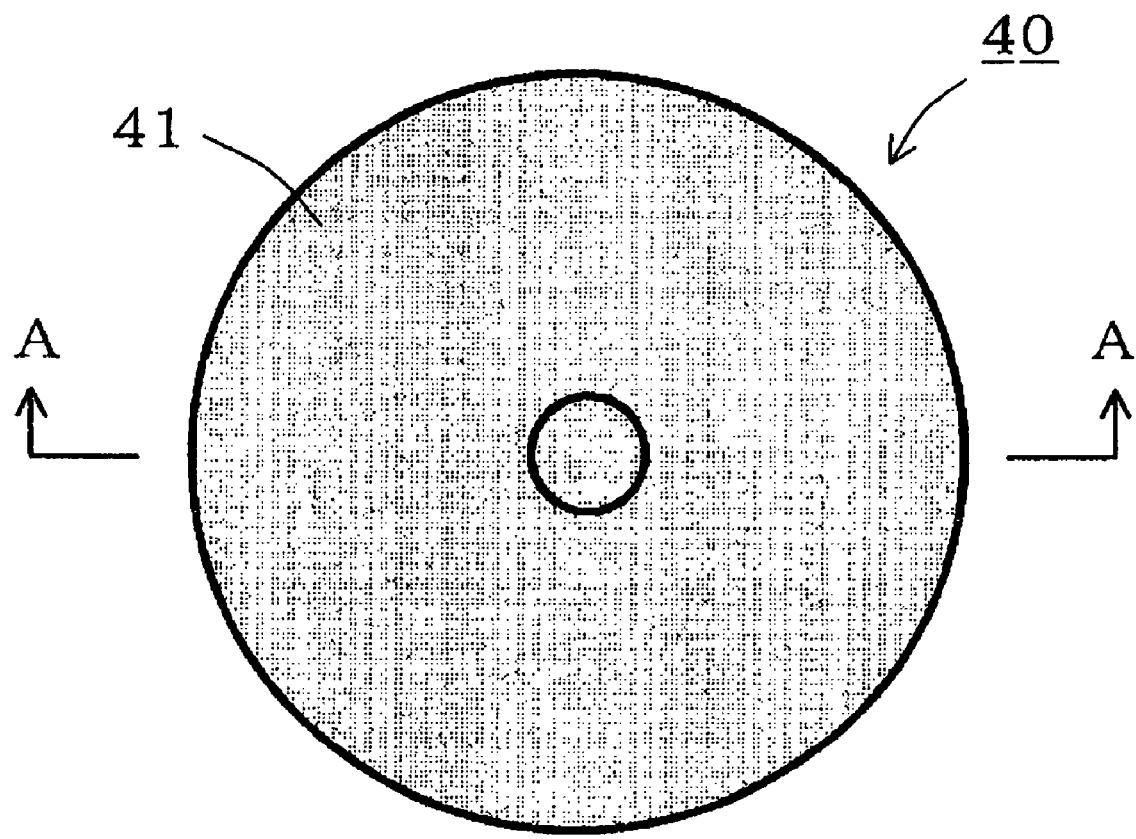
FIG. 6A is a plan view of an electrode member to be used for an iontophoresis device according to an embodiment.
Figure 6B:
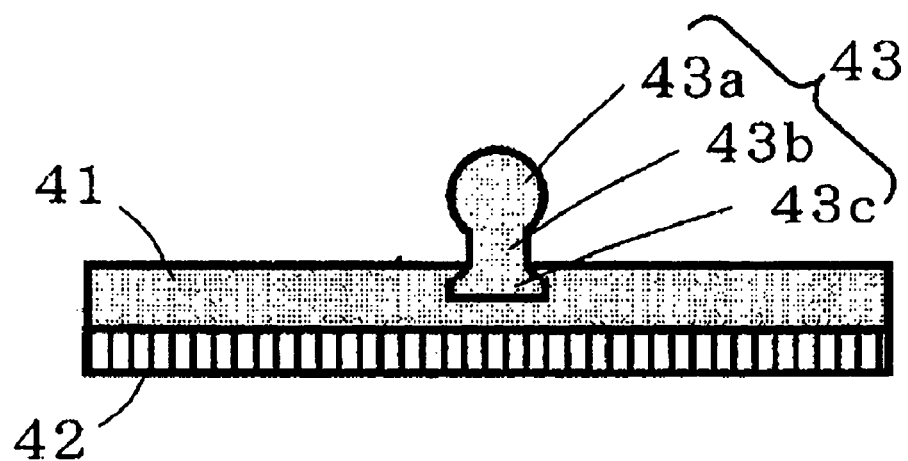
FIG. 6B is a sectional view taken along the line A-A of FIG. 6A.

FIG. 6A is a plan view of a polarizable electrode 40 that may be used as the electrode member 11 of each of the active electrode assemblies 10A to 10I or as the electrode member 21 of each of the counter electrode assemblies 20A to 20D, and FIG. 6B is a sectional view taken along the line A-A of FIG. 6A.

In the figures, reference numeral 41 denotes a collector comprising a carbon fiber, and a polarizable electrode 42 is formed on one surface of the collector 41.

The polarizable electrode 42 can include a member having, for example, planer shape and containing any one of a conductive material having a capacitance per unit weight of 1 F/g or greater, a conductive material having a specific surface area of 10 m²/g or greater, and activated carbon.

In a preferred configuration, the polarizable electrode 42 is obtained by forming, for example, a composition, which is prepared by blending 95 parts by weight of activated carbon powder having a specific surface area of approximately 100 $m^2/g$ with 5 parts by weight of polytetrafluoroethylene, into a membrane shape. In one configuration, the polarizable electrode 42 comprises an activated carbon fiber which is obtained by carbonizing and activating a novolid fiber.

A terminal member 43 comprising a male fitting portion 43*a*, a body portion 43*b*, and a joining portion 43*c* is attached to the other surface of the collector 41.

The terminal member 43 is obtained by hardening, in a die placed on the collector 41, a composition prepared by blending a polymer matrix such as silicone rubber with graphite, black lead, carbon black, or a carbon filler such as fine powder of glass-like carbon or a short fiber obtained by cutting a carbon fiber, through heating and vulcanization. The composition is hardened when immersed in a carbon fiber constituting the collector 41, whereby the collector 41 and the terminal member 43 are integrated with each other at the joining portion 43*c*.

The electrode member 40 enables energization from the polarizable electrode 42 at a uniform current density because a carbon fiber has high conductivity and high flexibility. As a result, the active electrode assemblies 10A to 10I and the counter electrode assemblies 20A to 20D each have enough flexibility to conform to the movement of a subject or the irregularities of the biological interface of the subject can be realized.

In addition, connection from the electric power source 30 to the electric supply lines 31 and 32 can be performed by using a connector having a female fitting portion that fits into the male fitting portion 43*a*. Even if a metallic material is used for the female fitting portion, the metal of the connector is prevented from eluting to transfer to a subject because the male fitting portion 43*a* is separated from the collector 41 by the body portion 43*b*.

Figure 6C:
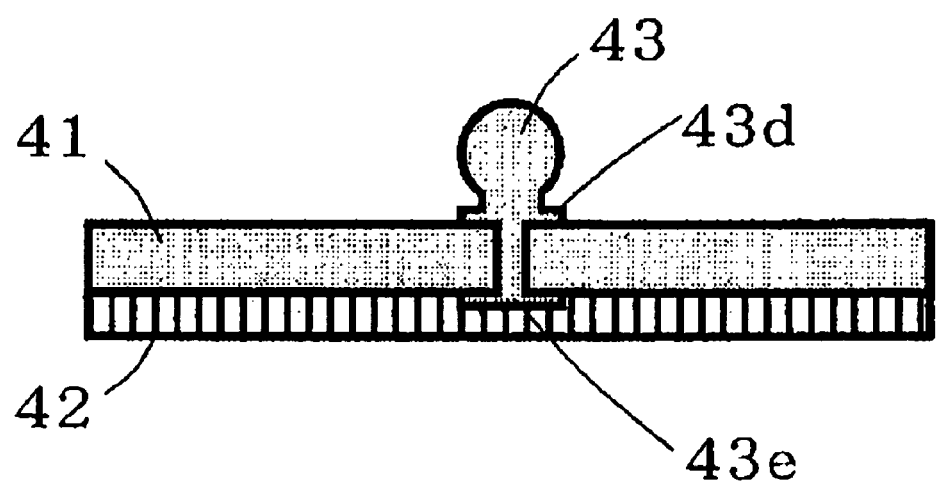
FIG. 6C is a sectional view showing a modification of FIG. 6B.

The terminal member 43 may be attached to the collector 41 by using any variety of methods. For example, as shown in FIG. 6C, the attachment can be performed by: forming engaging portions 43*d* and 43*e* on the terminal member 43; and inserting the engaging portion 43*e* into a small pore or aperture arranged on the collector 41.

Figure 7A:
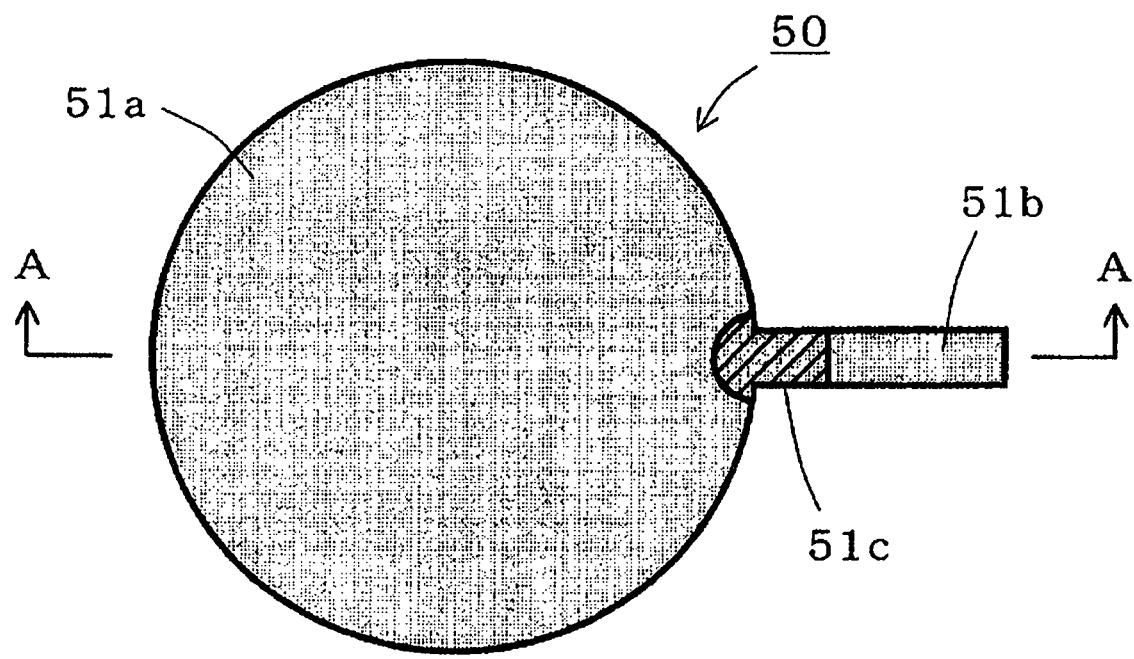
FIG. 7A is a plan view of an electrode member to be used for an iontophoresis device according to an embodiment.
Figure 7B:
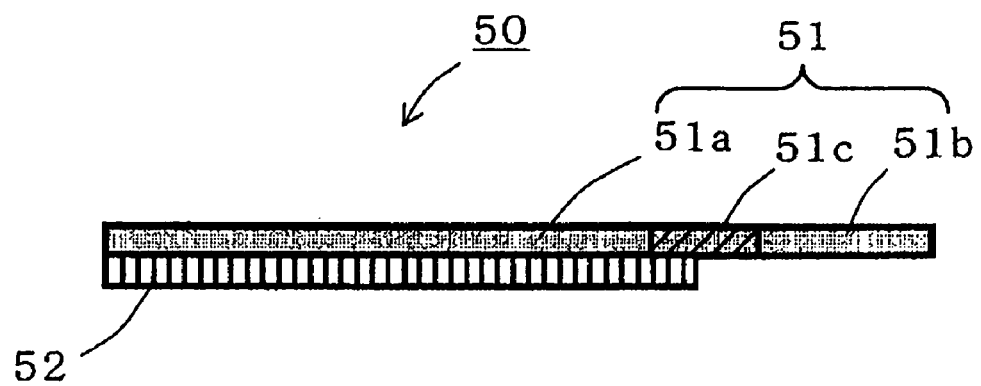
FIG. 7B is a sectional view taken along the line A-A of FIG. 7A.

FIG. 7A is a plan view of a polarizable electrode 50 according to another aspect that may be used as the electrode member 11 of each of the active electrode assemblies 10A to 10I or as the electrode member 21 of each of the counter electrode assemblies 20A to 20D, and FIG. 7B is a sectional view taken along the line A-A of FIG. 7A.

In the figures, reference numeral 51 denotes a collector comprising a carbon fiber and having a circular conductive sheet portion 51*a* and an elongated extension portion 51*b* extending from the conductive sheet portion 51*a*. A polarizable electrode 52 similar to the polarizable electrode 42 is formed on one surface of the conductive sheet portion 51*a*.

The electrode member 50 enables energization from the polarizable electrode 52 at a uniform current density as in the case of the electrode member 40. As a result, the active electrode assemblies 10A to 10I and the counter electrode assemblies 20A to 20D each have enough flexibility to follow the movement of a subject or the irregularities of the biological interface of the subject can be realized.

Figure 7C:
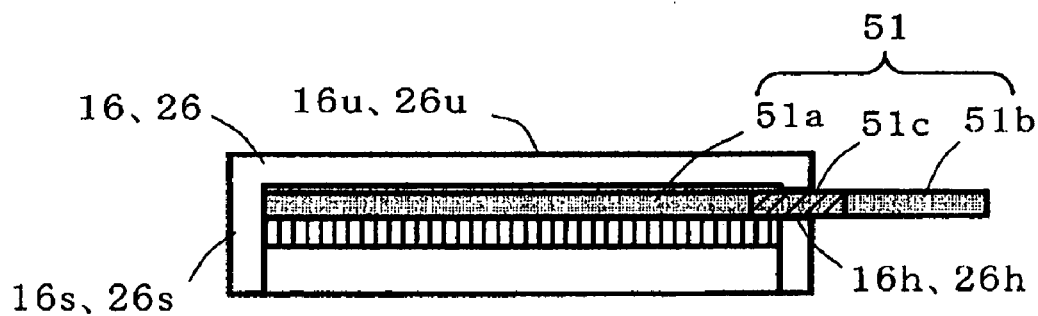
FIG. 7C is a sectional view showing a state where the electrode is housed in a container.

As shown in FIG. 7C, the electrode member 50 is used in combination with the container 16/26 having an opening 16*h*/26*h* formed on the outer peripheral wall 16*s*/26*s* or the upper wall 16*u*/26*u*, and is housed in the container 16/26 when the extension portion 51*b* is led from the opening 16*h*/26*h*.

Connection from the electric power source 30 to the electric supply lines 31 and 32 can be performed at the led extension portion 51*b* by using a connector, for example, an alligator clip attached to the tip of each of the electric supply lines 31 and 32.

In the case of an iontophoresis device housing therein a member having a high water content such as the electrolyte solution reservoir 12 or 22, or the active agent solution reservoir 14 like the active electrode assemblies 10A to 10G and the counter electrode assembly 20D, a water repellent portion 51*c* impregnated with a fluorine based resin, a silicone based resin, a silane based resin, or the like to provide water repellency is arranged at the extension portion 51*b* placed at the opening 16*h* or 26*h*. As a result, water may be prevented from leaking from an active electrode assembly or a counter electrode assembly. Alternatively, when a metallic member is used for the connector such as an alligator clip, a metal ion eluted from the member may be prevented from penetrating into an active electrode assembly or a counter electrode assembly.

The collectors 41 and 51 of the electrode member 40 and 50 may also be formed of carbon fiber paper. The carbon fiber or carbon fiber paper of the collector 41 or 51 may be impregnated with a soft polymer such as silicone rubber or thermoplastic polyurethane, whereby a reduction in quality of an electrode due to the failing of a carbon fiber can be prevented, and the handleability of the electrode member 40 or 50 can be improved.

Figure 8:
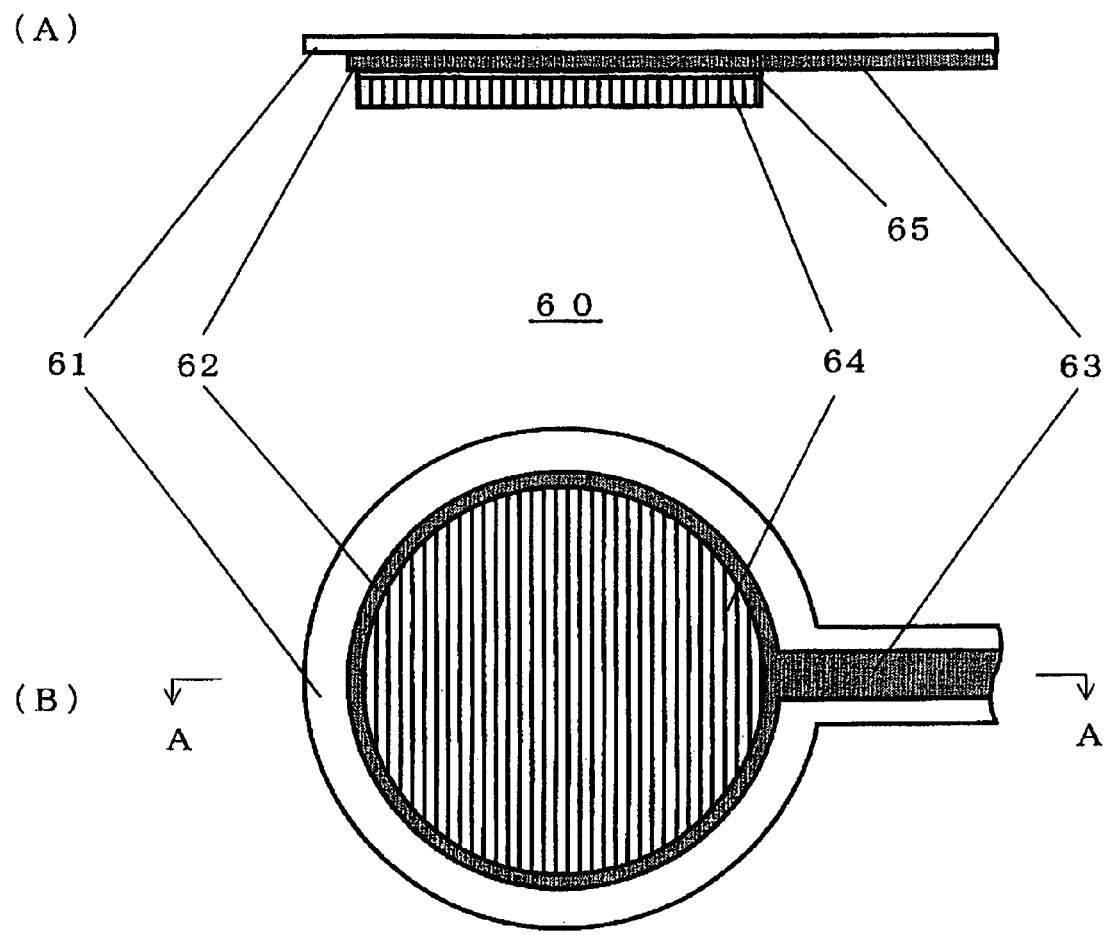
FIG. 8A is a plan view of an electrode member to be used for an iontophoresis device according to an embodiment.
FIG. 8B is a sectional view taken along the line A-A of FIG. 8A.

FIG. 8A is a plan view of an electrode member 60 according to another aspect that may be used as the electrode member 11 of each of the active electrode assemblies 10A to 10I or as the electrode member 21 of each of the counter electrode assemblies 20A to 20D, and FIG. 8B is a sectional view taken along the line A-A of FIG. 8A.

As shown, the electrode member 60 comprises a substrate 61 as a support member, a circularly shaped collector 62 formed on the substrate 61, a supply line 63 extending outwardly from the collector 62 and a polarizable electrode 65 formed on the collector 62.

The substrate 61 is typically a thin film member made of a plastic material and having a thickness of about 0.02 to 0.2 mm. PET film may be used for the substrate 61 in view of its flexibility and low cost.

The collector 62 and the supply line 63 can be a conductive coating film formed by painting or printing a conductive paint or ink containing a conductive powder on the substrate 61 and having a thickness of about 0.02 to 0.2 mm.

A thermosetting paint or ink may be used for the conductive paint or ink. In this case, chemically stable coating film can be obtained. It is possible to utilize a gold powder or a silver powder for the conductive powder in the conductive paint or ink. However, it is particularly preferable to utilize a carbon powder to suppress or eliminate the possibility that a metallic ion eluted from the collector 62 is transferred to a subject.

The supply line 63 can be connected at an extension end (not shown) to a terminal of the electric power source 30 by using a soldering or a conductive adhesive.

The polarizable electrode 64 can have the same configuration as the polarizable electrode 42. In the example shown in the figure, the area of the polarizable electrode 64 is slightly smaller than that of the collector 62. However, it is also possible for the area of the polarizable electrode 64 to be similar in size to that of the collector 62, or to be larger than that of the collector 62.

The polarizable electrode 64 can be made to adhere to the collector 62 by using a conductive adhesive to enhance conductivity from the collector 62 to the polarizable electrode 64.

The electrode member 60 may comprise inexpensive and easily available materials. Further, the electrode member 60 can be fabricated with a method suitable for automation or mass production, such as punching or coating of a conductive paint. Costs may thus be reduced.

The above description of illustrated embodiments, including what is described in the Abstract, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied to other delivery devices and methods, not necessarily the exemplary iontophoresis delivery devices and methods generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety.

Aspects of the embodiments can be modified, if necessary, to employ systems, circuits, structures, and concepts of the various patents, applications, and publications to provide yet further embodiments.

For example, the specific shape and dimensions of the electrode assembly, the polarizable electrode, and the like are shown merely as examples. The shapes and dimensions shown in the embodiments are not limiting.

Further, in each of the above embodiments, a collector is utilized to provide energization from a polarizable electrode at a uniform current density is described. However, the collector is not necessary, and it is also possible to configure an electrode member only with a polarizable electrode.

Further in each of the above embodiments, a single active electrode assembly and a single counter electrode assembly are utilized. However, it is also possible that a plurality of active electrode assembly and/or a plurality of counter electrode assembly are utilized. In this case, it is possible to configure an iontophoresis device by combining one or greater of any of the active electrode assemblies 10A to 10I and one or greater of any of the counter electrode assemblies 20A to 20D.

Figure 9:
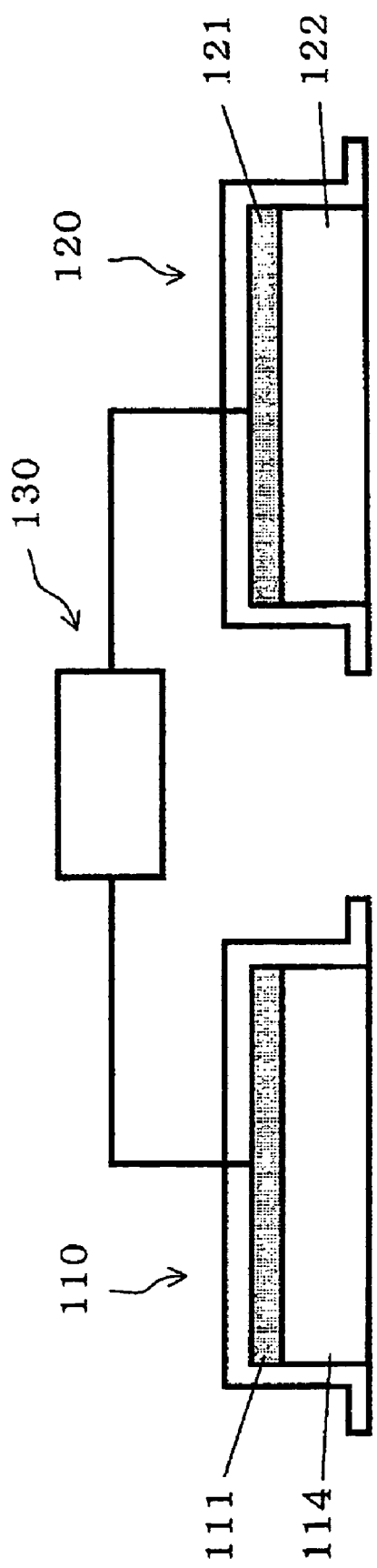
FIG. 9 is an explanatory view showing the configuration of a conventional iontophoresis device.
Figure 10:
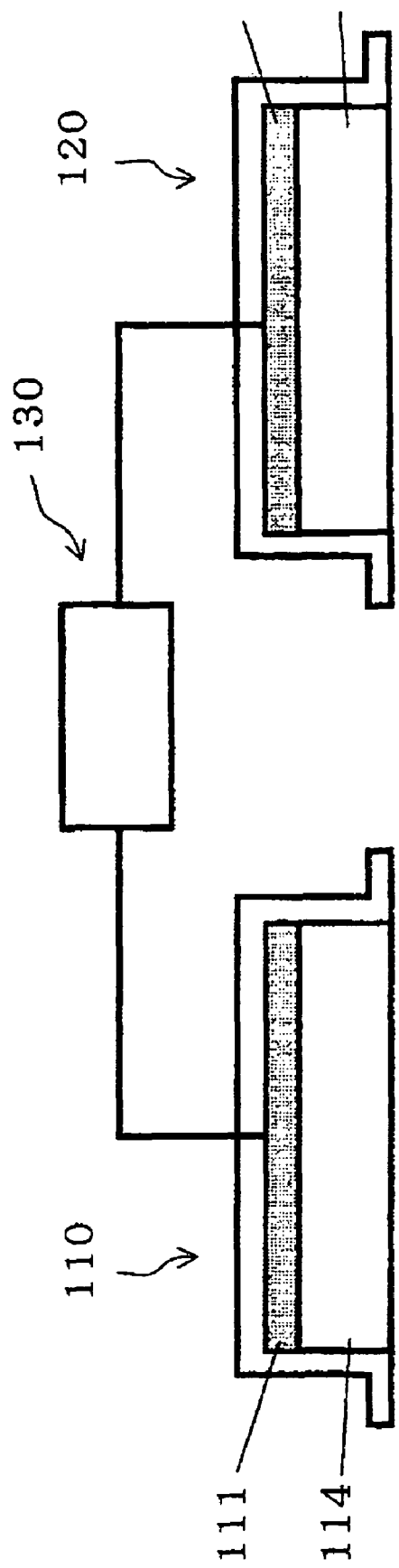
FIG. 10 is an explanatory view showing the configuration of another conventional iontophoresis device.

Further in each of the above embodiments, a case where each of the active electrode assembly 10 and the counter electrode assembly 20 includes a polarizable electrode. However, it is also possible that either one of the active electrode assembly 10 or the counter electrode assembly 20 does not include a polarizable electrode. In this case, it is possible to configure an iontophoresis device by combining one or greater of any of the active electrode assemblies 10A to 10I and one or greater of any of the counter electrode assembly 120 or 210 shown in FIG. 9 or 10. Alternatively, it is also possible to configure an iontophoresis device by combining one or greater of any of the counter electrode assemblies 20A to 20D and one or greater of any of the active electrode assembly 110 or 210 shown in FIG. 9 or 10.

Alternatively, an active agent can be administered as follows. If any one of the active electrode assemblies 10A to 10I is used, the iontophoresis device itself is provided with no counter electrode assembly, and, for example, an electrical potential may be applied to the active electrode assembly when the active electrode assembly is brought into contact with the biological interface of a subject and a part of the subject is brought into contact with a member to serve as the ground. The suppression of the generation of: oxygen gas, hydrogen gas, chlorine gas, or the like; and hydrogen ions, hydroxide ions, and hypochlorous acid in the active electrode assembly upon energization may be observed.

Furthermore, in each of the above embodiments, a description has been given of the case where the active electrode assembly, the counter electrode assembly, and the electric power source are separate. It is also possible that those elements are incorporated in a single casing or an entire device incorporating the assemblies is formed in a sheet shape or a patch shape, whereby the handleability thereof is enhanced, and such iontophoresis device is also included in the scope.

These and other changes can be made to the embodiments in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the scope of the invention shall only be construed and defined by the scope of the appended claims.

What is claimed is:

1. An iontophoresis device for administering active agent ions to a living body, comprising:
    an electrolyte solution holding part to hold an electrolyte solution comprising a plurality of first electrolytic ions of a first polarity and a plurality of second electrolytic ions of a second polarity opposite to the first polarity; and
    an electrode assembly comprising a polarized electrode, the polarized electrode comprising an electrical double layer, the electrical double layer including a conductive material having a capacitance per unit weight of 1 F/g or greater.

2. The iontophoresis device according to claim 1 wherein the polarized electrode is impregnatable with the electrolyte solution.

3. The iontophoresis device according to claim 1 wherein the polarized electrode is blended with a binder polymer.

4. The iontophoresis device according to claim 1 wherein:
    the electrode assembly further comprises a collector having an outer surface side; and
    the polarized electrode is located on the outer surface side of the collector.

5. The iontophoresis device according to claim 1 wherein the electrode assembly further comprises an active agent solution reservoir for holding an active agent solution containing an active agent ion, the active agent solution reservoir located on an outer surface side of the polarized electrode.

6. The iontophoresis device according to claim 1 wherein the electrode assembly further comprises a first ion exchange membrane comprising an active agent ion, the first ion exchange membrane located on an outer surface side of the polarized electrode.

7. An iontophoresis device, comprising:
    an electrode assembly comprising a polarized electrode, the polarized electrode comprising an electrical double layer, the electrical double layer including a conductive material having a specific surface area of 10 $m^2$/g or greater.

8. The iontophoresis device according to claim 7 wherein the polarized electrode holds an electrolyte solution.

9. The iontophoresis device according to claim 7 wherein the polarized electrode comprises a binder polymer.

10. The iontophoresis device according to claim 7 wherein:
the electrode assembly further comprises a collector having an outer surface side; and
the polarized electrode is located on the outer surface side of the collector.

11. The iontophoresis device according to claim 7 wherein the electrode assembly further comprises an active agent solution reservoir configured to hold an active agent solution containing an active agent ion, the active agent solution reservoir located on an outer surface side of the polarized electrode.

12. The iontophoresis device according to claim 11 wherein the polarized electrode holds an active agent solution having the same composition as that of an active agent solution in the active agent solution reservoir.

13. The iontophoresis device according to claim 12 wherein the electrode assembly further comprises a first ion exchange membrane comprising an active agent ion, the first ion exchange membrane located on the outer surface side of the polarized electrode.

14. The iontophoresis device according to claim 11 wherein the electrode assembly further comprises a first ion exchange membrane comprising an active agent ion, the first ion exchange membrane located on the outer surface side of the polarized electrode.

15. The iontophoresis device according to claim 7 wherein the electrode assembly further comprises a first ion exchange membrane comprising an active agent ion, the first ion exchange membrane located on an outer surface side of the polarized electrode.

16. An iontophoresis device, comprising:
an electrode assembly comprising a polarized electrode, the polarized electrode comprising an electrical double layer, the electrical double layer including activated carbon.

17. The iontophoresis device according to claim 16 wherein the polarized electrode holds an electrolyte solution.

18. The iontophoresis device according to claim 16 wherein the polarized electrode is blended with a binder polymer.

19. The iontophoresis device according to claim 18 wherein the binder polymer comprises polytetrafluoroethylene or polyvinylidene fluoride.

20. The iontophoresis device according to claim 18 wherein:
the electrode assembly further comprises a collector; and
the polarized electrode is located on an outer surface side of the collector.

21. The iontophoresis device according to claim 16 wherein:
the electrode assembly further comprises a collector; and
the polarized electrode is located on an outer surface side of the collector.

22. The iontophoresis device according to claim 21 wherein the electrode assembly further comprises an active agent solution reservoir configured to hold an active agent solution containing an active agent ion, the active agent solution reservoir located on the outer surface side of the polarized electrode.

23. The iontophoresis device according to claim 22 wherein the electrode assembly further comprises a first ion exchange membrane comprising an active agent ion, the first ion exchange membrane located on the outer surface side of the polarized electrode.

24. The iontophoresis device according to claim 21 wherein the collector comprises carbon fiber or carbon fiber paper.

25. The iontophoresis device according to claim 24 wherein the electrode assembly further comprises an active agent solution reservoir configured to hold an active agent solution containing an active agent ion, the active agent solution reservoir located on the outer surface side of the polarized electrode.

26. The iontophoresis device according to claim 25 wherein the electrode assembly further comprises a first ion exchange membrane comprising an active agent ion, the first ion exchange membrane located on an outer surface side of the polarized electrode.

27. The iontophoresis device according to claim 21 wherein the polarized electrode comprises a binder polymer.

28. The iontophoresis device according to claim 27 wherein the binder polymer comprises polytetrafluoroethylene or polyvinylidene fluoride.

29. The iontophoresis device according to claim 28 wherein the electrode assembly further comprises an active agent solution reservoir configured to hold an active agent solution containing an active agent ion, the active agent solution reservoir located on the outer surface side of the polarized electrode.

30. The iontophoresis device according to claim 29 wherein the electrode assembly further comprises a first ion exchange membrane comprising an active agent ion, the first ion exchange membrane located on the outer surface side of the polarized electrode.

31. The iontophoresis device according to claim 27 wherein the polarized electrode holds an electrolyte solution.

32. The iontophoresis device according to claim 16 wherein the activated carbon comprises an activated carbon fiber.

33. The iontophoresis device according to claim 32 wherein the activated carbon fiber is obtained by carbonizing and activating a novoloid fiber.

34. The iontophoresis device according to claim 32 wherein the polarized electrode holds an electrolyte solution.

35. The iontophoresis device according to claim 32 wherein the electrode assembly further comprises an active agent solution reservoir configured to hold an active agent solution containing an active agent ion, the active agent solution reservoir located on the outer surface side of the polarized electrode.

36. The iontophoresis device according to claim 35 wherein the electrode assembly further comprises a first ion exchange membrane comprising an active agent ion, the first ion exchange membrane located on an outer surface side of the polarized electrode.

37. The iontophoresis device according to claim 16 wherein the electrode assembly further comprises an active agent solution reservoir configured to hold an active agent solution containing an active agent ion, the active agent solution reservoir located on the outer surface side of the polarized electrode.

38. The iontophoresis device according to claim 37 wherein the electrode assembly further comprises a first ion exchange membrane comprising an active agent ion, the first ion exchange membrane located on the outer surface side of the polarized electrode.

39. The iontophoresis device according to claim 21 further comprising:
a terminal member comprising a conductive resin, the conductive resin comprising a polymer matrix and a carbon powder, the terminal member attached to the collector.

40. The iontophoresis device according to claim 21 wherein:
  the polarized electrode is blended with a binder polymer; and
  the collector is impregnated with a binder polymer.

41. The iontophoresis device according to claim 21 wherein the collector has a conductive sheet portion having a predetermined area and an extension formed integrally with the conductive sheet portion.

42. The iontophoresis device according to claim 21 wherein the collector comprises a coating film of a conductive paint containing a conductive powder.

43. The iontophoresis device according to claim 42 wherein the conductive powder comprises a carbon powder.

44. The iontophoresis device according to claim 21 wherein the collector and the polarized electrode are bonded to each other by using a conductive adhesive.

45. The iontophoresis device according to claim 21 wherein the collector is formed on a plastic substrate.

46. The iontophoresis device according to claim 21 wherein the electrode assembly further comprises an active agent solution reservoir configured to hold an active agent solution containing an active agent ion, the active agent solution reservoir located on the outer surface side of the polarized electrode.

47. The iontophoresis device according to claim 21 wherein the polarized electrode holds an active agent solution having the same composition as that of the active agent solution in the active agent solution reservoir.

48. The iontophoresis device according to claim 21 wherein the electrode assembly further comprises a first ion exchange membrane comprising an active agent ion, the first ion exchange membrane located on the outer surface side of the polarized electrode.

49. An iontophoresis device, comprising:
an active electrode assembly that holds an active agent ion of a first polarity;
a counter electrode assembly, the counter electrode assembly comprising a polarized electrode, the polarized electrode comprising an electrical double layer, the electrical double layer including a conductive material having a capacitance per unit weight of 1 F/g or greater; and
an ion exchange membrane located on an outer surface side of the polarized electrode.

50. An iontophoresis device, comprising:
an active electrode assembly that holds an active agent ion of a first polarity;
a counter electrode assembly, the counter electrode assembly comprising a polarized electrode, the polarized electrode comprising an electrical double layer, the electrical double layer including a conductive material having a specific surface area of 10 $m^2$/g or greater; and
an ion exchange membrane located on an outer surface side of the polarized electrode.

51. An iontophoresis device, comprising:
an active electrode assembly that holds an active agent ion of a first polarity;
a counter electrode assembly, the counter electrode assembly comprising a polarized electrode, the polarized electrode comprising an electrical double layer, the electrical double layer including activated carbon; and
an ion exchange membrane located on an outer surface side of the polarized electrode.

* * * * *